United States Patent [19]

Greenlee et al.

[11] Patent Number: 5,006,511
[45] Date of Patent: Apr. 9, 1991

[54] DI- OR TRIPEPTIDE RENIN INHIBITORS CONTAINING LACTAM CONFORMATIONAL RESTRICTION IN ACHPA

[75] Inventors: William J. Greenlee, Teaneck, N.J.; Daniel F. Veber, Ambler; Peter D. Williams, Lansdale, both of Pa.

[73] Assignee: Merck & Co., Inc., Rahway, N.J.

[21] Appl. No.: 237,648

[22] Filed: Aug. 26, 1988

Related U.S. Application Data

[63] Continuation of Ser. No. 108,343, Oct. 14, 1981, abandoned.

[51] Int. Cl.$^5$ .................. A61K 37/02; C07K 5/02; C07F 209/54; C07D 207/12
[52] U.S. Cl. .......................... 514/19; 514/18; 530/323; 530/331; 548/408; 548/344; 548/467; 548/550; 544/141; 544/139; 546/112; 546/208; 546/210
[58] Field of Search ............ 514/18, 19; 530/323, 530/331; 548/408, 467, 344; 544/139; 546/210, 112, 208

[56] References Cited

U.S. PATENT DOCUMENTS 4,384,994  5/1983  Veber et al. ............... 530/330
4,478,826 10/1984  Veber et al. ............... 514/16

*Primary Examiner*—Lester L. Lee
*Attorney, Agent, or Firm*—Charles M. Caruso; Mark R. Daniel

[57] ABSTRACT

Enzyme di- or tripeptides of the formula:

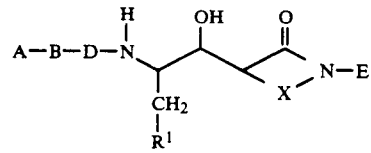

and analogs thereof which inhibit renin and are useful for treating various forms of renin-associated hypertension, hyperaldosteronism and congestive heart failure; compositions containing these renin-inhibitory peptides, optionally with other antihypertensive agents; and methods of treating hypertension, hyperaldosteronism or congestive heart failure or of establishing renin as a causative factor in these problems which employ these novel peptides.

9 Claims, No Drawings

DI- OR TRIPEPTIDE RENIN INHIBITORS CONTAINING LACTAM CONFORMATIONAL RESTRICTION IN ACHPA

This is a continuation of application Ser. No. 108,343, filed Oct. 14, 1987, now abandoned.

The present invention is concerned with novel di- or tripeptides which inhibit the angiotensinogen-cleaving action of the proteolytic enzyme, renin, with pharmaceutical compositions containing the novel peptides of the present invention as active ingredients, with methods of treating renin associated hypertension, hyperaldosteronism, and congestive heart failure, with diagnostic methods which utilize the novel peptides of the present invention, and with methods of preparing the novel peptides of the present invention.

BACKGROUND OF THE INVENTION

Renin is an endopeptidase (molecular weight about 40,000) produced and secreted by the juxtaglomerular cells of the kidney. Renin has a high specificity for and cleaves the naturally-occurring plasma glycoprotein, angiotensinogen, at only the 10, 11 peptide bond, i.e., between the 10th (Leu) and 11th (Leu) amino acid residues in the equine substrate, as described by Skeggs et al, *J. Exper. Med.* 1957, 106, 439, or between Leu 10 and Val 11 in the human renin substrate, as elucidated by Tewksbury et al., *Circulation* 59, 60, Supp. II: 132, Oct. 1979.

Cleavage of its protein substrate, angiotensinogen, by the aspartic proteinase, renin splits off the decapeptide, angiotensin I, which is thought to be hemodynamically-inactive, but which is converted in the lungs, kidney or other tissue by angiotensin converting enzyme (ACE) to the potent pressor octapeptide, angiotensin II. Angiotensin II then causes constriction of the arterioles and is also believed to stimulate release of the sodium-retaining hormone, aldosterone, from the adrenal gland, thereby causing a rise in extracellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin-angiotensin system. Consequently, specific inhibitors of the catalytic and rate-limiting enzymatic step that ultimately regulates angiotensin II production, the action of renin on its substrate, have also been sought as effective investigative tools, as well as therapeutic agents in the treatment of hypertension and congestive heart failure.

Renin antibody, pepstatin, phospholipids, and substrate analogs, including tetrapeptides and octa- to tridecapeptides, with inhibition constants ($K_i$) in the $10^{-3}$ to $10^{-6}$M region, have been studied.

Umezawa et al., in *J. Antibiot. (Tokyo)* 23: 259–262, 1970, reported the isolation of a peptide, pepstatin, from actinomyces that was an inhibitor of aspartyl proteases such as pepsin, cathepsin D, and renin. Gross et al., *Science* 175:656, 1972, reported that pepstatin reduces blood pressure in vivo after the injection of hog renin into nephrectomized rats. However, pepstatin has not found very wide application as an experimental agent because of its limited solubility and its inhibition of a variety of other acid proteases in addition to renin.

Many efforts have been made to prepare a specific renin inhibitor based on pig renin substrate analogy, since such analogy has been shown to correlate well with and predict human renin inhibitor activity. The octapeptide amino acid sequence extending from histidine-6 through tyrosine-13

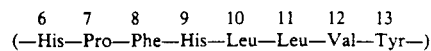

has been shown to have kinetic parameters essentially the same as those of the full tetradecapeptide renin substrate.

Kokubu et al., *Biochem. Pharmacol.*, 22, 3217–3223, 1973, synthesized a number of analogs of the tetrapeptide found between residues 10 to 13, but while inhibition could be shown, inhibitory constants were only of the order of $10^{-3}$M. Analogs of a larger segment of renin substrate have been also synthesized, e.g., Burton et al., *Biochemistry* 14: 3892–3898, 1975, and Poulsen et al., *Biochemistry* 12: 3877–3882, 1973, but a lack of solubility and weak binding (large inhibitory constant) generally resulted.

Modifications to increase solubility soon established that the inhibitory properties of the peptides are markedly dependent on the hydrophobicity of various amino acid residues. These modifications also established that increasing solubility by replacing lipophilic amino acids with hydrophilic isosteric residues can become counterproductive. Other approaches to increasing solubility have also had limited success.

Modifications designed to increase binding to renin have also been made, but here too, with mixed results.

A series of inhibitors of renin have been disclosed which contain the unnatural amino acid, statine: see, e.g., Veber et al, U.S. Pat. Nos. 4,384,994 and 4,478,826; Evans et al, U.S. Pat. No. 4,397,786; Boger et al, *Nature*, 1983, 303, 81–84 and U.S. Pat. Nos. 4,470,971; 4,485,099; 4,663,310 and 4,668,770; Matsueda et al, EP-A 128 762, 152 255; Morisawa et al., EP-A 186 977; Riniker et al, EP-A 111 266; Bindra et al, EP-A 155 809; Stein et al, *Fed. Proc.* 1986, 45, 869; and Hölzemann et al, German Offenlegungsschrift DE 3438545. Attempting to explain the effect of statine, Powers et al., in *Acid Proteases, Structure, Function and Biology*, Plenum Press, 1977, 141–157, observed that in pepstatin, statine occupies the space of the two amino acids on either side of the cleavage site of a pepsin substrate and Tang et al., in *Trends in Biochem. Sci.*, 1:205–208 (1976) and *J. Biol. Chem.*, 251:7088–94, 1976, pointed out that the statine residue of pepstatin resembles the transition state for pepsin hydrolysis of peptide bonds.

Renin inhibitors containing other peptide bond isosteres, including a reduced carbonyl isostere have been disclosed by M. Szelke et al, in work described in published European Patent Applications 45 665 and 104 041; in U.S. Pat. No. 4,424,207, and in PCT Int. Appl. WO 84/03044; in *Nature*, 299, 555 (1982); *Hypertension*, 4, Supp. 2, 59, 1981; and British Patent 1,587,809. In *Peptides, Structure and Function: Proceedings of the Eighth American Peptide Symposium*, ed. V. J. Hruby and D. H. Rich, p. 579, Pierce Chemical Co., Rockford, Ill., 1983, Szelke et al also showed isosteric substitutions at the Leu-Leu site of cleavage, resulting in compounds with excellent potency. These and other peptide bond isosteres have also been disclosed in Buhlmayer et al in EP-A 144 290 and 184 550; Hester et al, EP-A 173 481; Raddatz, EP-A 161 588; Dann et al, *Biochem. Biophys. Res. Commun.* 1986, 134, 71–77; Fuhrer et al, EP-A 143 746; Kamijo et al, EP-A 181 110; Thaisrivongs et al, *J.*

Med. Chem., 1985, 28, 1553-1555; Ryono et al., EP-A 181 071; and Evans et al, U.S. Pat. No. 4,609,641.

Other modifications which have been tried include preparing renin inhibitors with non-peptide C-termini, such as disclosed in European Published Applications 172 346 and 172 347; Evans et al, *J. Med. Chem.*, 1985, 28, 1755-1756; Bock et al, *Peptides, Structure and Function: Proceedings of the Ninth American Peptide Symposium,* ed. C. M. Deber et al, pp.751-754, Pierce Chemical Co., Rockford, Ill., 1985; and Plattner et al, in *Abstracts from the 191st National Meeting of the Anerican Chemical Society,* April, 1986. Kokubu et al, in *Hypertension,* 1985, 7, Suppl. I, p. 8-10 and Matsueda et al, in *Chemistry Letters,* 1985, 1041-1044 and in European Published Applications 128 762 and 152 255 disclosed peptide aldehyde renin inhibitors, and Hanson et al in *Biochem. Biophys. Res. Commun.* 1985, 132, 155-161, reported peptide glycol inhibitors.

These various renin inhibitors all generally comprise peptide based inhibitors in which a sequence of the type: ... A-B-D-E-F-G-J-K-L ..., where G is a peptide bond mimic and A,B,D,E,F,J,K, and L may individually be absent or may represent naturally-occuring or modified amino acids. Typical sequences of this type include:

```
        7    8    9   10   11   12
   ...BOC—Pro—Phe—His—Sta—Leu—Phe...,
``` or

```
        8    9   10   11
   ...BOC—Phe—His—Sta—Leu...,
``` where the N-terminus typically comprises an amino acid protecting group such as BOC or CBZ, and the N-terminal amino acids are Pro-Phe-His or Phe-His.

Lower molecular weight renin inhibitory di- or tripeptides comprising acyclic 2-substituted-4-amino-5-cyclohexyl-3-hydroxy-pentanoic acid (ACHPA) have been disclosed in U.S. patent application Ser. No. 45,941, filed May 4, 1987, and other lower molecular weight peptides have been disclosed in Sham, EP 184 855, Bindra et al, EP 155 809, and Matsueda et al, EP 152 255.

It was an object of this invention to prepare lower molecular weight peptides which have enhanced biological potency in inhibiting the renin enzyme. It was also an object to prepare shortened peptide sequences which incorporate at the C-terminus a stabilizing, conformationally-constrained dipeptide mimic to replace the 10-and 11-position amino acids in the analogous natural substrate. It was a further object to include strategically-located substituents at the C- and/or N-terminii of a shortened peptide which confer increased potency while constructively altering the physical properties of these peptides. It was an additional object of this invention to prepare peptides which have greater oral bioavailability and increased duration of action. It was still a further object of this invention to prepare novel peptides which are more useful antihypertensive agents, and compounds useful in treating hyperaldosteronism and congestive heart failure.

DETAILED DESCRIPTION OF THE INVENTION

The present invention is directed to renin-inhibitory di- and tripeptides of the structure:

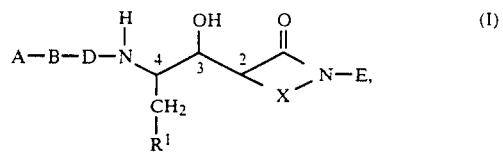

wherein:

A is hydrogen; $C_1$-$C_6$-alkyl; aryl, where aryl is unsubstituted or mono-, di- or trisubstituted phenyl, wherein the substituent(s) is/are independently selected from the group consisting of $C_1$-$C_7$-alkyl, phenyl $C_1$-$C_4$-alkyl, amino, mono- or di-$C_1$-$C_4$-alkylamino, amino $C_1$-$C_4$-alkyl, hydroxy-$C_1$-$C_4$-alkyl, mono or di-$C_1$-$C_4$-alkylamino-$C_1$-$C_4$-alkyl, guanidyl, guanidyl $C_1$-$C_4$-alkyl, hydroxyl, $C_1$-$C_4$-alkoxy, trifluoromethyl, halo, CHO, —$CO_2H$, —$CONH_2$, —CONH-$C_1$-$C_4$-alkyl, —CON($C_1$-$C_4$-alkyl)$_2$, —CO-$C_1$-$C_4$-alkyl, —$(CH_2)_m$—$^\oplus N(R^3)_2R^4$ $A^\ominus$, where $R^3$ is $C_1$-$C_4$-alkyl, —$(CH_2)_4$—, —$(CH_2)_5$— or —$(CH_2)_2$—$O$—$(CH_2)_2$—; $R_4$ is $C_1$-$C_4$-alkyl, $C_1$-$C_4$-hydroxyalkyl, $C_1$-$C_4$-carboxyalkyl, or —$CH_2$-phenyl; $A^\ominus$ is a counterion selected from the group consisting of single negatively-charged ions, such as chloride, bromide, perchlorate, benzoate, benzene sulfonate, tartrate, maleate, hemitartate, and acetate; and m is 0-to-3; —$CO_2$-$C_1$-$C_4$-alkyl, -$CO_2$-$C_1$-$C_4$-alkoxy-$C_2$-$C_4$-alkyl,

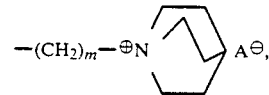

where $A^\ominus$ and m are as defined above, and —$NR^5R^6$, where $R^5$ and $R^6$ are independently hydrogen, unsubstituted or monosubstituted $C_1$-$C_4$-alkyl, wherein the substituent is amino, mono- or di-$C_1$-$C_4$-alkylamino or —$^\oplus N(R^3)_2R^4$ $A^\ominus$, where $R^3$, $R^4$ and $A^\ominus$ are as defined above; Het, where Het is an unsubstituted or mono- or disubstituted 5-to-7-membered mono or bicyclic or 7-to-10-membered bicyclic heterocyclic ring, where the one or two heteroatoms are independently selected from the group consisting of N, O, S, NO, SO, $SO_2$ or quaternized N, and the substituent(s) is/are independently selected from the group consisting of hydroxyl, thiol, $C_1$-$C_6$-alkyl, $CF_3$, $C_1$-$C_4$-alkoxy, halo, aryl, as defined above, aryl-$C_1$-$C_4$-alkyl, amino, mono- or di-$C_1$-$C_4$-alkylamino, amino-$C_1$-$C_4$-alkyl, hydroxy-$C_1$-$C_4$-alkyl, mono- or di-$C_1$-$C_4$-alkylamino-$C_1$-$C_4$-alkyl, guanidyl, guanidyl-$C_1$-$C_4$-alkyl, CHO, $CO_2H$, $CO_2$-$C_1$-$C_4$-alkyl, $CONH_2$, CONH-$C_1$-$C_4$-alkyl, CON($C_1$-$C_4$-alkyl)$_2$, $NR^5R^6$,

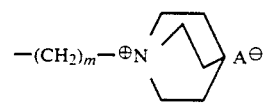

and —$(CH_2)_m$—$^\oplus N(R^3)_2R^4$ $A^\ominus$, wherein $R^5$, $R^6$, $A^\ominus$, m, $R^3$ and $R^4$ are as defined above, or when the heteroatom N is present, the substituents are alternatively —$(CH_2)_q$— or —$(CH_2)_2$—O—$(CH_2)_2$— and form a quaternary spirocyclic ring with the N-atom, wherein q is 3-to-6;

where $R^2$ is $C_1$-$C_7$-alkyl; hydrogen; Het, as defined above; aryl, as defined above; mono-substituted $C_1$-$C_5$-alkyl, wherein the substituent is selected from the group consisting of aryl, as defined above; Het, as defined above; hydroxyl; —$CO_2H$; $CO_2R^7$, where $R^7$ is $C_1$-$C_5$-alkyl, aryl, as defined above, and aryl-$C_1$-$C_4$-alkyl; $CONH_2$; —CONH—$R^7$ or —S(O)$_n$—$R^7$, wherein n is 0-to-2 and $R^7$ is as defined above; $C_1$-$C_4$-alkoxy; $C_3$-$C_7$-cycloalkyl; amino; mono- or di-$C_1$-$C_4$-alkylamino; —NH-aryl, —NH—$CH_2$-aryl or —CO-aryl, where aryl is as defined above; and —NH-Het, —NH—$CH_2$-Het or -CO- Het, where Het is as defined above;

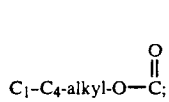

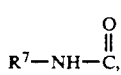

where $R^7$ is as defined above; or

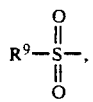

where is $R^9$ is $C_1$-$C_5$-alkyl, aryl, as defined above, or Het, as defined above;

B and D are independently

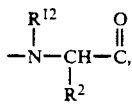

where $R^{12}$ is hydrogen, $C_1$-$C_5$-alkyl or $CH_2$-aryl, wherein aryl is as defined above; and $R^2$ is as defined above;

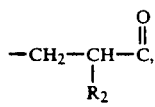

where $R^2$ is as defined above; or either B or D, but not both simultaneously, is absent;

$R^1$ is hydrogen; $C_3$-$C_6$-alkyl; aryl, as defined above; unsubstituted, mono-, di- or trisubstituted $C_3$-$C_7$-cycloalkyl, where the substituent(s) is/are selected from the group consisting of $C_1$-$C_4$-alkyl, trifluoromethyl, hydroxyl, $C_1$-$C_4$-alkoxy and halo; or unsubstituted or 4-monosubstituted 1,3-dithiolan-2-yl or unsubstituted or 4-mono-substituted 1,3-dithian-2-yl, where the substituent is —$(CH_2)_m$-aryl, where m and aryl are as defined above;

X is

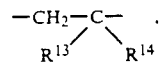

where $R^{13}$ and $R^{14}$ are independently hydrogen; $C_1$-$C_7$-alkyl; $C_2$-$C_7$-alkenyl; —$CO_2H$; —$CONH_2$; —$CO_2R^7$, —CO—NH—$R^7$ or —CO—N($R^7$)$_2$, wherein $R^7$ is as defined above; monosubstituted $C_1$-$C_5$-alkyl, wherein the substituent is selected from the group consisting of azido; halo; hydroxy; $C_1$-$C_5$-alkoxy; aryl, aryl-$CH_2O$—, aryloxy, aryl-COO—, aryl-$CH_2$—NH— or arylamino, where aryl is as defined above; $C_1$-$C_5$-alkyl-$CO_2$—; $R^7NH$—COO—, $R^7$—CO—NH—, $R^7$—NH—CO—NH— or $R^7$—S-(O)$_n$, where n and $R^7$ are as defined above; amino; mono- or di-$C_1$-$C_4$-alkylamino; or Het, as defined above; or $R^{13}$ and $R^{14}$ are connected to form a polymethylene chain of the formula, —$(CH_2)_p$, where p is 2-to-6; or

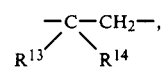

and where $R^{13}$ and $R^{14}$ are as defined above; and

E is hydrogen; aryl, as defined above; Het, as defined above; $C_2$-$C_7$-alkenyl; or unsubstituted or monosubstituted $C_1$-$C_7$-alkyl or unsubstituted or monosubstituted $C_3$-$C_7$-cycloalkyl, where the substituent is selected from the group consisting of aryl, —CO-aryl, —NH-aryl or —O-aryl, wherein aryl is as defined above; Het, —NH-Het, —O-Het, —CO-Het, —NH—CO-Het, CO—NH-Het, —CO—NH $CH_2$-Het or O—CO-Het, wherein Het is as defined above; azido; $C_3$-$C_7$-cycloalkyl; halo; hydroxyl; $C_1$-$C_4$-alkoxy; —COOH; —O—CO—$R^7$, —O—CO—NH—$R^7$, —NH—CO—$R^7$, —NH—CO—NH—$R^7$, —S(O)$_n$—$R^7$, —$CO_2R^7$ or —CO—NH—$R^7$, wherein $R^7$ and n are as defined above; amino; mono- or di-$C_1$-$C_4$-alkylamino; —CHO; and —⊕N($R^3$)$_2R^8$ A⊖,

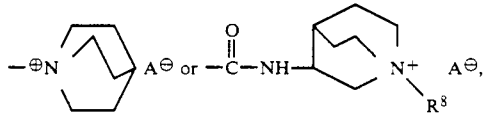

where $R^8$ is $C_1$-$C_4$-alkyl, $C_1$-$C_4$-hydroxy-alkyl, $C_1$-$C_4$ carboxyalkyl, —$CH_2$-aryl, wherein aryl is as defined above, or —$CH_2$-Het, wherein Het is as defined above, and $R^3$ and A⊖ are as defined above; and pharmaceutically-acceptable salts thereof.

In the peptides of the present invention, the components having asymmetric centers occur as racemates, racemic mixtures and as individual diastereomers, with all isomeric forms generally being included in the present invention. In particular, asymmetric carbon atoms at the 2, 3 and 4 positions in peptides of Formula I preferably have an S configuration.

When any variable (e.g., aryl, Het, m, n, $R^2$, $R^3$, $R^7$, A$^-$, etc.) occurs more than one time in any variable or in formula I, its definition on each occurrence is independent of its definition at every other occurrence.

As used herein, "alkyl" is intended to include both branched and straight chain saturated aliphatic hydrocarbon groups having the specified number of carbon atoms (Me is methyl, Et is ethyl); "alkoxy" represents an alkyl group of indicated number of carbon atoms attached through an oxygen bridge; and "$C_3$-$C_7$-cycloalkyl" is intended to include saturated ring groups, such as cyclopropyl, cyclobutyl, cyclopentyl, cyclohexyl and cycloheptyl. "Alkanoyl" is intended to include those alkylcarbonyl groups of specified number of carbon atoms, which are exemplified by formyl, acetyl, propanoyl and butanoyl; "alkenyl" is intended to include hydrocarbon chains of either a straight- or branched- configuration and one unsaturation, which may occur at any point along the chain, such as ethenyl, propenyl, butenyl, pentenyl, and the like, and includes E and Z forms, where applicable; and "arylalkyl" represents aryl groups as herein defined which are attached through a straight- or branched- chain alkyl group of specified number of carbon atoms, such as, for example, benzyl, phenethyl, 3,3-diphenylpropyl, 3-indolymethyl, and the like. "Halo", as used herein, means fluoro, chloro, bromo and iodo, and "counterion" is used to represent a small, single negatively charged specie, such as chloride, bromide, hydroxide, nitrate, acetate, benzoate, perchlorate, benzene sulfonate, tartrate, hemitartrate, maleate, and the like.

As used herein, with exceptions as noted, "aryl" is intended to mean phenyl (Ph), which is optionally substituted by from one- to three- members independently selected from the group consisting of $C_1$-$C_7$-alkyl, amino (Am), mono- or di-$C_1$-$C_4$-alkylamino, phenyl-$C_1$-$C_4$-alkyl, amino-$C_1$-$C_4$ alkyl, hydroxy-$C_1$-$C_4$ alkyl, mono- or di-$C_1$-$C_4$-alkyamino-$C_1$-$C_4$-alkyl, hydroxyl, guanidyl, guanidyl $C_1$-$C_4$-alkyl, $C_1$-$C_4$-alkoxy, $CF_3$, halo, CHO, $CO_2H$, $CONH_2$, CONH -$C_1$-$C_4$-alkyl, $CON(C_1$-$C_4$-alkyl)$_2$, CO-$C_1$-$C_4$-alkyl or $(CH_2)_m$—$^{\oplus}N(R^3)_2R^4$ $A^{\ominus}$, wherein $R^3$, $R^4$ and m are as defined above and $A^{\ominus}$ is counterion, as defined herein. "Aroyl" is intended to include those aryl-carbonyl groups which are exemplified by phenoyl.

The term "Het", as used herein, represents a 5-to-7-membered mono or bicyclic or 7-to-10-membered bicyclic hetrocyclic ring which is either saturated or unsaturated, and which consists of carbon atoms and one or two heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined 5-to-7-membered monocyclic heterocyclic rings is fused to a benzene ring. Heterocycles which contain nitrogen are preferred. In the case of a heterocyclic ring containing one or more nitrogen atoms, the point of attachment may be at one of the nitrogen atoms, or at any carbon atom. Examples of such heterocyclic elements include piperidyl, piperidinyl, piperazinyl, 2-oxopiperazinyl, 2-oxopyrolodinal, 2-oxopiperidinyl, 2-oxoazepinyl, azepinyl, pyrryl, pyrrolinyl, 4-piperidonyl, pyrrolidinyl, pyrazolyl, pyrazolinyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, benzothiazolyl, benzoxazolyl, furyl, thienyl, benzothienyl, thiamorpholinyl, thiamorpholinyl sulfoxide, and thiamorpholinyl sulfone. The heterocyclic moiety is further optionally substituted by from one- to four-members independently selected from the group consisting of hydroxyl, thiol, $C_1$-$C_6$-alkyl, $CF_3$, $C_1$-$C_4$-alkoxy, halo, aryl, aryl-$C_1$-$C_4$-alkyl, amino, mono- or di-$C_1$-$C_4$alkylamino, amino $C_1$-$C_4$-alkylamino, amino-$C_1$-$C_4$ alkyl, hydroxy-$C_1$-$C_4$-alkyl, mono- or di-$C_1$-$C_4$-alkylamino-$C_1$-$C_4$-alkyl, guanidyl, guanidyl-$C_1$-$C_4$-alkyl, CHO, $CO_2H$, $CO_2C_1$-$C_4$-alkyl, $CONH_2$, CONH-$C_1$-$C_4$-alkyl, $CON(C_1$-$C_4$-alkyl)$_2$, —$NR^5R^6$,

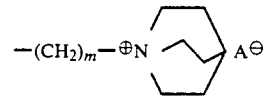

or —$(CH_2)_m$—$^{\oplus}N(R^3)_2R^8$ $A^{\ominus}$, wherein $R^5$, $R^6$, $A^{\ominus}$, m, $R^3$ and $R^8$ are as defined above, and including spiro quaternary species.

The following additional abbreviations have also been used herein:

| Abbreviated Designation | |
|---|---|
| | Amino Acid/Residue |
| ACHPA | (3S,4S)-4-amino-5-cyclohexyl-3-hyroxypentanoic acid |
| Ala | L-alanine |
| Arg | L-arginine |
| Cys | cysteine |
| Gly | L-glycine |
| His | D- or L-histidine |
| HomoPhe | homologated phenylalanine |
| HomoTrp | homologated tryptophan |
| HomoTyr | homologated tyrosine |
| Ile | L-isoleucine |
| Leu | L-leucine |
| Lys | L-lysine |
| Met | L-methionine |
| Nle | norleucine |
| Nva | norvaline |
| Orn | L-ornithine |
| (p-MeO)Phe | L-para-methoxyphenylalanine |
| Phe | L-phenylalanine |
| Pro | proline |
| Sar | L-sarcosine (N-methylglycine) |
| Ser | L-serine |
| Sta | statine |
| Thr | L-threonine |
| Trp | L-tryptophan |
| Tyr | L-tyrosine |
| Val | L-valine |
| | Protecting Group |
| BOC | t-butyloxycarbonyl |
| CBZ | benzyloxycarbonyl(carbobenzoxy) |
| DNP | 2,4-dinitrophenyl |
| IPOC | isopropoxycarbonyl |
| | Activating Group |
| HBT(HOBt) | 1-hydroxybenzotriazole hydrate |
| HOSU | N-hydroxysuccinimide |
| | Condensing Agent |
| DCCI (DCC) | dicyclohexylcarbodiimide |
| DPPA | diphenylphosphorylazide |
| EDC | 1-(3-dimethylaminopropyl)-3-ethyl-carbodiimide hydrochloride |
| | Reagent |
| (BOC)$_2$O | di-sd,5 t butyl dicarbonate |
| DIBAL | diisobutylaluminum hydride |
| DIPEA | diisopropylethylamine |
| DMAP | 4-(dimethylamino)pyridine |
| TEA | triethylamine |
| TFA | trifluoroacetic acid |
| LAH | lithium aluminum hydride |
| LDA | lithium diisopropylamide |
| MCPBA | 3-chloroperoxybenzoic acid |
| NMM | N-methyl morpholine |
| PPTS | pyridinium para-toluenesulfonate |
| TBAF | tetra-n-butylammonium fluoride |
| | Solvent |

| Abbreviated Designation | |
|---|---|
| HOAc (AcOH) | acetic acid |
| DMF | dimethylformamide |
| DMSO | dimethyl sulfoxide |
| EtOAc | ethyl acetate |
| EtOH | ethanol |
| Et₂O | ether |
| MeOH | methanol |
| THF | tetrahydrofuran |

The novel renin inhibitory peptides of the present invention may be generalized and alternately described in terms of common amino acid components and closely-related analogs thereof, in accordance with formula I, wherein
A, $R^1$, X and E are as defined under Formula I;
B is Absent, Ala, Leu, Phe, HomoPhe, (p-MeO)Phe, Tyr, Trp, HomoTrp or

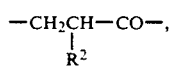

where $R^2$ as defined above;
D is Absent, Ala, Ser, Met, Thr, Phe, Tyr, Trp, His, Lys, Orn, Arg or Val, such that B and D are not simultaneously absent.

In terms of substrate analogy, a unique aspect and essential feature of the present invention is the substitution of the

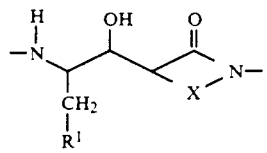

component for the double amino acid sequence, Leu¹⁰-Val¹¹ in the endogenous human renin substrate

```
 7    8    9    10   11   12   13
(Pro  Phe  His  Leu  Val  Ile  His),
``` which substitution for both amino acids at the cleavage site rather than just one is believed to result in an improved substrate analogy and better fit to the renin enzyme. This invention's peptides particularly comprise novel lactam versions of rigid 4-amino-5-cyclohexyl-3-hydroxy-pentanoic acid (ACHPA), which enables stereospecific placement of substituents, and allows the

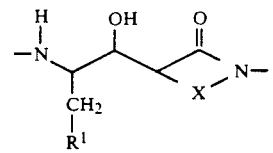

component to better mimic the Leu¹⁰-Val¹¹ dipeptide moiety in the natural substrate.

It will be understood that closely related analogs of the above common amino acids, for example, aliphatic amino acids in addition to Ala, Val, Leu, and Ile, such as α-aminobutyric acid (Abu), substituted phenyl derivatives of Phe, and $N^\alpha$-methyl amino acids, are included in the broad description of the novel inhibitory peptides of the present invention represented by Formula I and related definitions.

Preferred renin-inhibitory peptides are those wherein A is $R^2$—CO—, $R^9$—SO₂-, $C_1$-$C_4$-alkyl-13 O—CO-13 - or $R^7$—NH—CO—, wherein $R^2$, $R^7$ and $R^9$ are as defined above; B is absent (when D is present), L-phenylalanyl or derivatives thereof substituted on the aromatic ring by para-methoxy, or

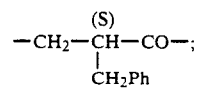

D is absent (when B is present), L-histidyl or L-valinyl; $R^1$ is cyclohexyl; X is

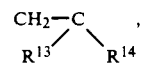

wherein $R^{13}$ and $R^{14}$ are simultaneously or independently hydrogen, methyl, ethenyl or ethyl; and E is $C_1$-$C_6$-alkyl, —(CH₂)ᵣ—⊕N(R³)₂R⁸ CH₃CO₂⁻, wherein r is 2 or 3 and $R^3$ and $R^8$ are as defined above,

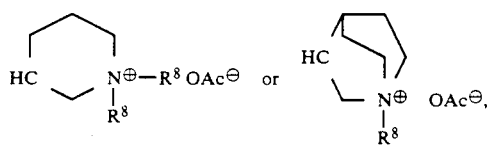

wherein $R^8$ is as defined above. The preferred stereochemistry at the 2,3 and 4 positions is S.

Representative preferred renin-inhibitory peptides of the present invention include the following compounds having the structure:

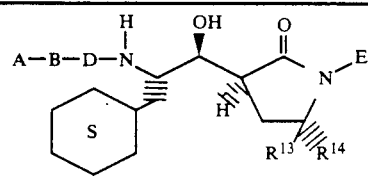

wherein, in the structures:

| | A | B | D | R¹³ | R¹⁴ | E |
|---|---|---|---|---|---|---|
| 1. | (CH₃)₃C—CO— | Phe | His | H | H | n-Bu |
| " | " | " | " | " | " | —CH₂—CH(CH₃)₂ |
| " | " | " | " | " | " | —CH₂—CH(CH₃)—CH₂CH₃ |

-continued

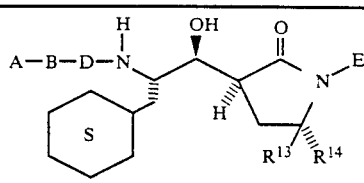

wherein, in the structures:

| A | B | D | R¹³ | R¹⁴ | E |
|---|---|---|---|---|---|
| " | " | " | —CH=CH₂ | " | n-Bu |
| 5. (CH₃)₃C—CO— | " | " | —CH₃ | " | " |
| " | " | " | " | —CH₃ | " |
| (CH₃)₂CH—SO₂— | " | " | " | " | " |
| O\_/N—CO— | " | " | " | " | " |
| — | indole-2-CO— | " | " | " | " |
| 10. (CH₃)₂CH—SO₂— | —CH₂—CH(CH₂Ph)—CO— (S) | His | —CH₃ | —CH₃ | n-Bu |
| (CH₃)₃C—CO— | Phe | " | " | " | (CH₂)₂—N⁺(Et)₂CH₂Ph OAc⁻ |
| (CH₃)₂CH—SO₂— | " | " | " | " | " |
| " | CH₂CH(CH₂Ph)—CO— (S) | " | " | " | " |
| " | " | Val | " | " | " |
| O\_/N—CO— | Phe | His | " | " | " |
| 15. | | | | | |
| (CH₃)₃C—CO— | " | " | " | " | (CH₂)₃N⁺(Et)₂—CH₂Ph OAc⁻ |
| (CH₃)₂CH—SO₂— | " | " | " | " | " |
| " | CH₂CH(CH₂Ph)—CO— (S) | " | " | " | " |
| " | " | Val | " | " | " |
| O\_/N—CO— | Phe | His | " | " | " |
| 20. | | | | | |
| (CH₃)₃C—CO— | Phe | His | H | H | —HC(piperidine-N⁺(Et)₂) OAc⁻ |
| (CH₃)₂CH—SO₂— | " | " | " | " | " |

-continued

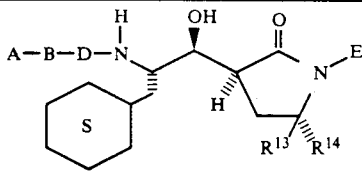

wherein, in the structures:

| | A | B | D | R¹³ | R¹⁴ | E |
|---|---|---|---|---|---|---|
| | " | —CH₂CH(CH₂Ph)—CO— (S) | His | " | " | " |
| | " | " | Val | " | " | " |
| | " | Phe | His | " | " | " |
| 25. | O(morpholine)N—CO— | " | " | " | " | " |
| | (CH₃)₃C—CO— | " | " | " | " | HC(piperidinyl)N⁺(CH₂Ph) ⊖OAc |
| | (CH₃)₂CH—SO₂— | " | " | " | " | " |
| | " | —CH₂CH(CH₂Ph)—CO— (S) | " | " | " | " |
| | O(morpholine)N—CO— | Phe | " | " | " | " |
| 30. | — | indole-2-CO— | His | H | H | HC(piperidinyl)N⁺(CH₂Ph) ⁻OAc |
| | — | " | " | " | " | —HC(piperidinyl)N⁺(Et)₂ ⊖OAc |
| | — | " | " | —CH₃ | —CH₃ | —(CH₂)₃—N⁺(Et)₂CH₂Ph OAc⊖ |
| 33. | — | " | " | " | " | —(CH₂)₂N⁺(Et₂)CH₂Ph OAc⊖ |

More preferred renin-inhibitory peptides include those wherein

| | A | B | D | R¹³ | R¹⁴ | E |
|---|---|---|---|---|---|---|
| 1. | Boc | Phe | His | H | H | —(CH₂)₂N⁺(Et)₂CH₃⊖OAc |
| | Ipoc | " | " | " | " | " |
| | (CH₃)₂CH—SO₂ | " | " | " | " | " |
| | " | —CH₂CH(CH₂Ph)—CO— (S) | " | " | " | " |
| 5. | Boc | Phe | " | CH₃ | CH₃ | " |

-continued

| A | B | D | R¹³ | R¹⁴ | E |
|---|---|---|-----|-----|---|
| Ipoc (CH₃)₂CH—SO₂ | " " | " " | " " | " " | " " |
| " | (S)<br>CH₂CH—CO—<br>    |<br>    CH₂Ph | " | " | " | " |
| " | " | " | " | " | n-Bu |
| " | " | " | " | " | 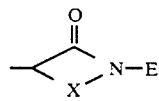 —HC⟨⟩N(Et)₂ ⊖OAc ⊕ |
| Ipoc (CH₃)₂CH—SO₂ | " " | " " | " " | " " | " " |
| " | (S)<br>CH₂CH—CO—<br>    |<br>    CH₂Ph | " | " | " | " |

The pharmaceutically-acceptable salts of the peptides of Formula I (in the form of water- or oil-soluble or dispersible products) include the conventional non toxic salts or the quarternary ammonium salts of these peptides which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Chemical synthesis of the compounds with the general structure given in formula I may be accomplished in several ways as illustrated by the following generalized procedures (wherein "ACHP", an abbreviation of 2-Amino-3-Cyclohexyl-1-HydroxyPropyl, is used in describing the structural segment which joins the A-B-D- and $$\underset{X}{\overset{O}{\underset{\|}{\diagup\!\!\diagdown}}}\!\!\diagdown_{N-E}$$

(pyrrolidinone) portions of the invention as shown in formula I. The ACHP segment is connected through the 1-position of the propyl chain to the 3-position of the pyrrolidinone, and through the amino group to the A-B D-segment.)

Method A

Step A1. A derivative of 2-pyrrolidinone is obtained through commercial sources or is prepared using well known chemical methods for preparation of members in this class (see Example 1);

Step A2. The enolate of the 2-pyrrolidinone derivative is generated, such as by using LDA as the base, and is added to a nitrogen-protected (e.g., N-Boc or N-CBZ protected) α amino aldehyde (e.g., N-tert-butyloxycarbonyl-cyclohexylalaninal) to give a Boc- or CBZ-protected amino alcohol derivative (see Example 2);

Step A3. The nitrogen protecting group of the amino alcohol derivative from step A2 is removed (e.g., by hydrogenolysis for CBZ protection, or TFA treatment for Boc protection) and the amine is coupled using standard peptide methodology to one or two amino acids, or to an appropriate carboxylic acid, the structure(s) of which is/are described by A, B, and D in the general formula I (e.g. see Example 3A steps 1 and 2, and Example 3B); and Step A4. Removal of any protecting groups which may have been used, e.g., on the lactam substituent(s) $R^{13}$, $R^{14}$, or E), or on the amino acid side chains (see Example 3A, step 3), gives the final products.

Method B

Steps A1 and A2 are followed.

Step B3. Modification of the lactam substituent(s) $R^{13}$, $R^{14}$, and E in generic formula I) is/are performed, as shown in Examples 2V-2PP.

Then Steps A3 and A4 are followed.

Method C

Steps A1, A2 and A3 are followed.

Step C4: Modification of the lactam substituent(s) $R^{13}$, $R^{14}$, and E in generic formula I) is/are performed, as shown in Examples 3H 3Q.

Step A4 is then followed.

The novel peptides of the present invention possess a high degree of activity in treating renin-associated hypertension, hyperaldosteronism and/or congestive heart failure in humans, as well as in other warm blooded animals such as mice, rats, horses, dogs and cats.

For these purposes, the peptides of the present invention may be administered orally, parenterally (including subcutaneous injections, intravenous, intramuscular, intrasternal injection or infusion techniques), by inhalation spray, or rectally, in dosage unit formulations containing conventional non-toxic, pharmaceutically-acceptable carriers, adjuvants and vehicles.

Thus, in accordance with the present invention there is further provided a method of treating and a pharmaceutical composition for treating renin-associated hypertension, hyperaldosteronism, and/or congestive heart failure. This treatment involves administering to a patient in need of such treatment a pharmaceutical composition comprising a pharmaceutical carrier and a therapeutically effective amount of a peptide of the formula:

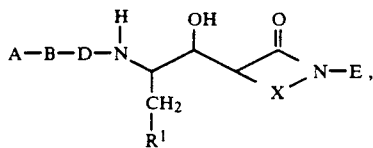

wherein A, B, D, R$^1$, X, and E are defined above, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions; or suppositories.

When administered orally as a suspension, these compositions may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared as solutions in saline, employing benzyl alcohol or other suitable preservatives, absorption promoters to enhance bioavailability, flourocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 2.0 grams-per-day are useful in the treatment of the above-indicated conditions, with oral doses two-to-five times higher.

For example, reninassociated hypertension and hyperaldosteronism are effectively treated by the administration of from 10 to 50 milligrams of the compound per kilogram of body weight from one to three times per day. It will be understood, however, that the specific dose level and frequency of dosage for any particular patient will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy.

The present invention is also directed to combinations of the novel renin-inhibitory peptides of Formula I with one or more antihypertensive agents selected from the group consisting of diuretics, α-and/or β-adrenergic blocking agents, CNS-acting agents, adrenergic neuron blocking agents, vasodilators, angiotensin I converting enzyme inhibitors, calcium channel blockers, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;

((±)-2-[3-(tert-butylamino)-2-hydroxypropoxy]-2-furananilide) (ancarolol);

(2-acetvl-7-(2-hydroxy-3-isopropylaminopropoxy)benzofuran HCl) (befunolol);

((±)-1-(isopropylamino)-3-(p-(2-cyclopropylmethoxyethyl)-phenoxy)-2-propranol HCl) (betaxolol);

(1-[(3,4-dimethox-yphenethyl)amino]-3-(m-tolyloxy)-2-propanol HCl) (bevantolol);

((±)-1-(4-((2-isopropoxyethoxy)methyl)phenoxy)-3-isopropylamino-2-propanol)fumarate) (bisoprolol);

(4-(2-hydroxy-3-[4-(phenoxymethyl) piperidino]-propoxy) indole);

(carbazolyl-4-oxy-5,2-(2-methoxyphenoxy)-ethylamino-2-propanol);

(1-((1,1-dimethylethyl)amino)-3-((2-methyl-IH-indol-4-yl)oxy)-2-propanol benzoate) (bopindolol);

(1-(2-exobicyclo[2.2.1]-hept-2-ylphenoxy)-3-[(1-methylethyl)-amino]-2-propanol HCl) (bornaprolol);

(o-[2-hydroxy 3-[(2-indol-3-yl-1,1-dimethylethyl)-amino]propoxy]benzonitrile HCl) (bucindolol);

(α-[(tert.butylamino)methyl]-7-ethyl-2-benzofuranmethanol) (bufuralol);

(3-[3-acetyl-4-[3-(tert.butylamino)-2-hydroxypropyl]-phenyl]-1,1-diethylurea HCl) (celiprolol);

((±)-2-[2 [3-[(1,1-dimethylethyl)amino]-2-hydroxypropoxy]-phenoxy]-N methylacetamide HCl) (cetamolol);

(2-benzimidazolyl-phenyl(2-isopropylaminopropanol));

((±)3'-acetyl-4'-(2-hydroxy-3 isopropylaminopropoxy)-acetanilide HCl) (diacetolol);
(methyl-4-[2-hydroxy-3-[(1-methylethyl)aminopropoxy]]-benzenepropanoate HCl) (esmolol);
(erythro-DL-1-(7-methylindan-4-yloxy)-3-isopropylaminobutan-2-ol);
(1-(tert.butylamino)-3-[O-(2-propynyloxy)phenoxy]-2-propanol (pargolol);
(1-(tert.butylamino)-3-[o (6-hydrazino-3-pyridazinyl)phenoxy]-2 -propanol diHCl) (prizidilol);
((−)-2-hydroxy-5-[(R) 1 hydroxy 2 [(R)-(1 methyl-3-phenylpropyl)amino]ethyl]benzamide);
(4 hydroxy 9-[2-hydroxy-3 (isopropylamino)-propoxy]-7-methyl-5H furo[3,2-g][1]benzopyran-5-one) (iprocrolol);
((−)-5-(tert.butylamino)-2-hydroxypropoxy]-3,4-dihydro-1-(2H)-naphthalenone HCl) (levobunolol);
(4-(2-hydroxy-3-isopropylamino propoxy)-1,2-benzisothiazole HCl);
(4-[3-(tert.butylamino) 2-hydroxypropoxy]-N-methylisocarbostyril HCl);
((±)-N-2-[4-(2-hydroxy-3-isopropyl aminopropoxy)-phenyl]ethyl-N'-isopropylurea) (pafenolol);
(3-[[(2-trifluoroacetamido)ethyl]amino]-1 phenoxy-propan-2-ol);
(N-(3-(o-chlorophenoxy)-2-hydroxypropyl)-N'-(4'-chloro-2,3-dihydro-3-oxo-5-pyridazinyl)ethylenedia
((±)-N-[3-acetyl-4-[2-hydroxy-3-[(1-methylethyl)amino]-propoxy]phenyl]butanamide) (acebutolol);
((±)-4'-[3-(tert-butylamino)-2-hydroxy-ropoxy]spiro-[cyclohexane-1,2'-indan]-1'-one) (spirendolol);
(7-[3-[[2-hydroxy-3-[(2-methylindol-4-yl)oxy]propyl]-amino]butyl]thiophylline) (teoprolo);
((±)-1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert.butylamino) 2-hydroxypropoxy]-5-methyl-coumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone) (butofilolol);
(1-(carbazol-4-yloxy)-3(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadol);
((S)-1-(2-cyclopentylphenoxy)-3-[(1,1-dimethylethyl)-amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);

((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±)-6-[[2-[[3-(p butoxyphenoxy)-2-hydroxypropyl]-amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]-aminoethyl]hydantoin HCl);
(3,4-dihydro-8-(2-hydroxy-3-isopropylaminopropoxy)-3-nitroxy-2H-1-benzopyran) (nipradolol);
α- and β-Adrenergic Blocking Agents:
((±)-1-tert-butylamino)-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);
(4-hydroxy-α-[[3-(4-methoxyphenyl)-1-methylpropyl]-aminomethyl]-3-(methylsulfinyl)-benzmethanol HCl) (sulfinalol);
(5-[1-hydroxy-2-[[2-(o-methoxyphenoxy)ethyl]amino]-ethyl]-2-methylbenzenesulfonamide HCl);
(5-[1-hydroxy-2-[(1-methyl-3-phenylpropyl)amino]ethyl]-salicylamide HCl) (labetalol);
(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]-propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl)-4-piperidyl)-3,4-dihydroxy)quinoxolin-2(1H)-one);
CNS-Acting Agents: clonidine; methyldopa;
Adrenergic Neuron Blocking Agents: guanethidine; reserpine and other rauwolfia alkaloids such as rescinnamine;
Vasodilators: diazoxide; hydralazine; minoxidil;
Angiotensin I Converting Enzyme Inhibitors
1-(3-mercapto-2-methyl-1-oxopropyl)-L-proline (captopril);
(1-(4-ethoxycarbonyl-2,4(R,R)-dimethylbutanoyl)-indoline-2(S)-carboxylic acid);
(2-[2-[[1-(ethoxycarbonyl) 3-phenyl-propyl]amino]-1-oxopropyl]-1,2,3,4-tetrahydro-3-isoquinoline carboxylic acid);
((S)-1-[2-[[1-(ethoxycarbonyl)-3-phenylpropyl]amino]-1-oxopropyl]octahydro 1H-indole-2-carboxylic acid HCl);
(N-cyclopentyl N-(3-(2,2-dimsthyl-1-oxopropyl)thiol-2-methyl-1-oxopropyl)glycine) (pivalopril);
((2R,4R)-2-(2-hydroxyphenyl)-3-(3-mercaptopropionyl)-4-thiazolidinecarboxylic acid);
(1-(N-[1(S)-ethoxycarbonyl-3-phenylpropyl]-(S)-alanyl)-cis,syn-octahydroindol-2(S)-carboxylic acid HCl);
((−)-(S)-1-[(S)-3-mercapto-2-methyl-1-oxopropyl]-indoline-2-carboxylic acid);
([1(S),4S]-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro -2-oxo-1-(3S)-benzazepine-1-acetic acid HCl);

(N-(2-benzyl-3-mercaptopropanoyl)-S-ethyl-L-cysteine) and the S-methyl analogue;

(N (1(S)-ethoxycarbonyl-3-phenylpropyl)-L-alanyl-L-proline maleate) (enalapril);

N-[1-(S)-carboxy-3-phenylpropyl]-L-alanyl-1-proline;

$N^2$-[1-(S) carboxy-3-phenylpropyl]-L-lysyl-L-proline (lisinopril);

Calcium Channel Blockers

α-[3-[[2-(3,4-dimethoxyphenyl)ethyl]methylamino]-propyl]-3,4-dimethoxy-α-(1-methylethyl)benzeneacetonitrile (verapamil);

1,4-dihydro-2,6-dimethyl-4-(2-nitrophenyl)-3,5-pyridinedicarboxylic acid dimethyl ester (nifedipine);

2-(2,2-dicyclohexylethyl)piperidine (perhexiline);

N-(1-methyl-2-phenylethyl)-phenylbenzenepropanamine (prenylamine);

3-(aminosulfonyl)-4-chloro-N-(2,3-dihydro2-methyl-1H-indol-1-yl)benzamide (indapamide);

(2'-(2-diethylaminoethoxy)-3-phenylpropiophenone (etafenone);

(4-[4,4-bis-(4-fluorophenyl)butyl]-N-(2,6 dimethylphenyl)-1-piperazineacetamide) (lidoflazine);

(2-(N-benzyl-N-methylamino)ethylmethyl-2,6-dimethyl-4-(m-nitrophenyl)-1,4-dihydro-3,5-pyridinedicarboxylate HCl) (nicardipine);

N-(3,4 dimethoxyphenethyl)-2-(3,4-dimethoxyphenyl)-N-methyl-m-dithiane-2-propylamine1,1,3,3-tetraoxide) (tiapamil);

(5,6-dimethoxy-2-(3-[(α(3,4-dimethoxy)phenylethyl)-methylamino]propyl)phthalimidine) (falipamil);

(β[(2-methylpropoxy)methyl]-N-phenyl-N-phenyl-methyl-1-pyrrolidineethanamine HCl monohydrate) (bepridil);

((+)-cis-3-(acetyloxy)-5-[2-(dimethylamino)ethyl]-2,3-dihydro-2-(4-methoxyphenyl)-1,5-benzothiazepin-4-(5H)-one) (diltiazem);

((E)-1-[bis-(p-fluorophenyl)methyl]-4-cinnamylpiperazine di HCl) (flunarizine);

(5-[(3,4-dimethoxyphenethyl)methylamino]-2-isopropyl-2-(3,4,5-trimethoxyphenyl)valeronitrile (gallopamil);

(ethylmethyl(2,3-dichlorophenyl)-1,4-dihydro-2,6-dimethyl-3,5-pyridinedicarboxylate (felodipine);

(isopropyl-2-methoxyethyl-1,4-dihydro-2,6-dimethyl-4-(3 nitrophenyl)-3,5-pyridinecarboxylate) (nimodipine);

(3-ethyl-5-methyl-1,4-dihydro-2,6-dimethyl-4-(3-nitrophenyl)-3,5-pyridine-dicarboxylate) (nitrendipine);

Other Antihypertensive Agents: aminophylline; cryptenamine acetates and tannates; deserpidine; meremethoxylline procaine; pargyline; trimethaphan camsylate; and the like, as well as admixtures and combinations thereof.

Typically, the individual daily dosages for these combinations can range from about one-fifth of the minimally-recommended clinical dosages to the maximum recommended levels for the entities when they are given alone. Coadministration is most readily accomplished by combining the active ingredients into a suitable unit dosage form containing the proper dosages of each. Other methods of coadministration are, of course, possible.

The renin-inhibitory novel peptides of the present invention may also be utilized in in vivo or in vitro diagnostic methods for the purpose of establishing the significance of renin as a causative or contributory factor in hypertension, hyperaldosteronism or congestive heart failure in a particular patient.

In the in vivo method, a novel peptide of the present invention is administered to a patient, preferably by intravenous injection, although parenteral administration is also suitable, at a hypotensive dosage level in a single dose of from 0.1 to 10 mg per kg of body weight, and the resulting transitory fall in blood pressure, if it occurs, indicates supranormal plasma renin levels.

In vitro methods which may be employed involve incubating a body fluid, preferably plasma, with a novel peptide of the present invention according to methods described in Boger et al., *J. Med. Chem.*, 1985, 28, 1779–1790.

The following are intended to exemplify the present invention, without, however, limiting it.

EXAMPLE 1

Synthesis of Starting Lactams

A. Preparation of 1-Allyl-2-Pyrrolidinone

To a suspension of NaH (14.1 g of a 60% suspension in mineral oil; 353 mmol) in degassed DMF (500 mL) was added 2-pyrrolidinone (25 g; 294 mmol) dropwise over a period of 10 min. The resulting suspension was stirred at room temperature for 6 hr. and then cooled to 0° C. Allyl bromide (42.8 g; 353 mmol) was added and the resulting mixture was stirred overnight, allowing the cooling bath to warm to room temperature.

Acetic acid (3 mL) was added to quench any remaining NaH and the volume of the mixture was reduced by one half on a rotovap (ca. 2 torr, bath temperature 30° C.). An equal volume of ether was added, the mixture was cooled in a refrigerator for several hours, and the salts were removed by filtration. The ether and the bulk of the remaining DMF were then removed under reduced pressure on the rotovap with more salt being precipitated by the addition of ether, and removed by filtration.

Solvent was removed from the filtrate under reduced pressure and the resulting oil was distilled from $CaH_2$ under reduced pressure. The resulting oil was distilled from $CaH_2$ under reduced pressure to give 1-allyl-2-pyrrolidinone as a colorless liquid (26.5 g; 72% yield; bp 53-55° C., 0.5 torr).

B. Preparation of 5(R)- or 5(S)-Benzyloxymethyl-1-Methyl-2-Pyrrolidinone

Step 1. 5(R)- or 5(S)-Carbomethoxy 1-Methyl-2-Pyrrolidinone

To a suspension of NaH (19.4 g of a 60% suspension in mineral oil; 0.484 mol) in degassed DMF (500 mL) under an atmosphere of nitrogen was added D-or L-pyro glutamic acid (25 g; 0.19 mol) portionwise over a period of 15 min. The resulting suspension was stirred at room temperature for 8 hr., at which time it was cooled to 0° C. Methyl iodide (69.7 g; 0.484 mol) was added, and the mixture was stirred overnight, allowing the cooling bath to warm to room temperature.

Acetic acid (3 mL) was added to quench any remaining NaH, and the bulk of the DMF was removed on the rotovap (vacuum pump pressure of approximately 2 torr, 30° C.). The thick precipitate of NaI was suspended in $CH_2Cl_2$ (100 mL) and cooled for several hours in the refrigerator. The salt was removed by filtration and washed with ether, with the volatile solvents being removed on the rotovap. The remaining DMF was removed by slow distillation under reduced pressure (0.5 torr) at 35° C. overnight.

The crude product (lower layer) was separated from mineral oil (upper layer) by means of a pipette and was flash chromatographed (SiO$_2$; 2%–5% MeOH/CH$_2$Cl$_2$) to give 5-carbomethoxy-1-methyl-2-pyrrolidinone as a nearly colorless liquid (24 g; 80% yield).

Step 2. 5(R)- or 5(S)-Hydroxymethyl-1 Methyl-2-Pyrrolidinone

To a mechanically-stirred −78° C. solution of 5(R)- or 5(S)-carbomethoxy-1-methyl-2pyrrolidinone (22.0 g; 0.140 mol) in dry THF (400 mL) under an atmosphere of nitrogen was added a solution of LAH (70 ml of a 1.0 M solution in THF; 70 mmol) dropwise over a period of 20 min. After being stirred for 1 hr. at −78° C., the cooling bath was removed and the stirring was continued for another 1.5 hr at which time the reaction was quenched by the addition of 7 mL of 10% aqueous NaOH solution, followed by 7 mL of water.

The resulting mixture was stirred for 2 hr., until a white precipitate had formed. This precipitate was removed by filtration and was washed with EtOAc, with the filtrate solvents being removed under reduced pressure. The resulting oil was purified by flash chromatography (SiO$_2$; 3%–7% MeOH/CH$_2$Cl$_2$) to obtain 5-hydroxymethyl-1-methyl-2-pyrrolidinone as a colorless oil (13.5 g; 75% yield).

Step 3. 5(R)- or 5(S)-Benzyloxymethyl-1-Methyl-2-Pyrrolidinone

To a suspension of NaH (2.42 g of a 60% suspension in mineral oil; 60.5 mmol) in dry THF (150 mL) under an atmosphere of nitrogen was added a solution of 5(R)- or 5(S)-hydroxymethyl-1-methyl-2-pyrrolidinone (6.50 g; 50.4 mmol) in dry THF (25 mL) over a period of 10 min. After being stirred at room temperature for 3 hr., the suspension was cooled to 0° C. and benzyl bromide (10.3 g; 60.5 mmol) was added. The mixture was stirred overnight, allowing the cooling bath to warm to room temperature.

Acetic acid (2 mL) was added to the mixture to quench any remaining NaH, and after the addition of ether (150 mL), NaBr was removed by filtration. The solvents were removed under reduced pressure and the oily residue was purified by flash chromatography (SiO$_2$; 35% EtOAc/CH$_2$Cl$_2$). 5-benzyloxymethyl-1-methyl-2-pyrrolidinone was obtained as a colorless liquid (10.6 g; 96% yield).

C. Preparation of 1-Methyl-5(R)- or 5(S)-Vinyl-2-Pyrrolidinone

To a −78° C. solution of oxallyl chloride (9.44 g; 74.3 mmol) in dry CH$_2$Cl$_2$ (200 mL) under an atmosphere of nitrogen was added DMSO (9.68 g; 124 mmol) dropwise over a period of 5 min. After being stirred for 15 min., a solution of 5(R)- or 5(S)-hydroxymethyl-1-methyl-2-pyrrolidinone (8.00 g; 62.0 mmol) in dry CH$_2$Cl$_2$ (15 mL) was added dropwise over a period of 5 min. The resulting solution was stirred at −78° C. for 30 min., at which time Et$_3$N (15.5 g; 153 mmol) was added.

The cooling bath was removed and the mixture with its thick white precipitate was stirred for an additional 45 min. Ether (200 mL) was added and the mixture, after being cooled to 0° C. in an ice-water bath, was filtered through Celite with the filtercake being washed with ether. The filtrate was concentrated under reduced pressure on a rotovap, keeping the bath temperature at or below 30° C. and residual DMSO was removed at room temperature under reduced pressure (0.2 torr).

The crude aldehyde so obtained was dissolved in dry THF (40 mL) and added via cannula to a −78° C. solution of methylene triphenylphosphorane whose preparation (given below) was concurrent with the oxidation procedure described above. To a suspension of methyl triphenylphosphonium bromide (46.6 g; 131 mmol) in dry THF (250 mL) at −78° C. and under an atmosphere of nitrogen was added n-butyllithium (78 mL of a 1.6 M solution in hexane; 125 mmol). After being stirred for 30 min., the dry ice/acetone cooling bath was replaced with an ice-water bath and the bright yellow orange mixture was stirred at 0° C. for 1 hr., then re-cooled to −78° C. and stirred at that temperature throughout the time period required for the oxidation procedure described above.

After the aldehyde solution had been added, the reaction mixture was stirred at −78° C. for 6 hr. and was then allowed to gradually warm to room temperature over a period of 4 hr. Acetic acid (4 mL) was added to quench any remaining ylide, and the thick, pasty mixture was diluted with 2 volumes of ether and cooled in the refrigerator for several hours with the solids being removed by filtration. The filtercake was washed with ether and the filtrate was concentrated under reduced pressure and additional triphenylphosphine oxide was precipitated by cooling a CH$_2$Cl$_2$ solution (ca. 25 mL) of the crude product overnight in the refrigerator.

The next morning, the supernatant was decanted and the solids were washed with a cold solution of 1:1 ether:—CH$_2$Cl$_2$. The combined supernatant and washings were concentrated under reduced pressure and flash chromatographed (SiO$_2$; 2:15:85 MeOH/ether/CH$_2$Cl$_2$). The resulting liquid was further purified by bulb-to-bulb distillation (60° C. bath temperature; 0.1 torr) giving 1-methyl-5-vinyl-2-pyrrolidinone as a colorless liquid (3.40 g; 44% yield over two steps).

D. Preparation of 5(R)- or 5(S)-Methoxymethyl-1-Methyl-1-Pyrrolidinone

To a suspension of NaH (1.53 g of a 60% suspension in mineral oil; 38.1 mmol) in dry THF (200 mL) under an atmosphere of nitrogen was added 5(R)- or 5(S)-hydroxymethyl-1-methyl-2-pyrrolidinone (4.10 g; 31.8 mmol) as a solution in dry THF (15 mL). The resulting suspension was stirred at room temperature for 4 hr., at which time it was cooled to 0° C. and methyl iodide (5.45 g; 38.1 mmol) was added. The mixture was stirred overnight, allowing the cooling bath to warm to room temperature.

Acetic acid (1 mL) was added to quench any remaining NaH, and the mixture was diluted with one volume of ether and cooled for several hours in the refrigerator. The salts were removed by filtration and the filtrate was concentrated under reduced pressure, with the resulting oil being flash chromatographed (SiO$_2$; 2%–4% MeOH/CH$_2$Cl$_2$). The liquid which was obtained was further purified by bulb-to-bulb distillation (bath temperature 50° C.; 0.2 torr), giving 5-methoxymethyl-1-methyl-2-pyrrolidinone as a pale yellow liquid (3.72 g; 82% yield).

E. 5-Fluoromethyl-1-Methyl-2-Pyrrolidinone

5-Hydroxymethyl-1-methyl-2-pyrrolidinone (see step 2 of Example 1B) and trifluoromethanesulfonic anhydride are reacted in CH$_2$Cl$_2$ and pyridine at 0° C. to give the trifluoromethylsulfonate ester, which is treated with TBAF in THF solution to give the title compound.

F. O-(1-Methyl-2-Pyrrolidinone-5-yl)Methyl N-2-Propyl Urethane

5-Hydroxymethyl-1-methyl-2-pyrrolidinone (see step 2 of Example 1B) and 2-propylisocyanate are heated to reflux in THF solution to give the title compound.

G. 5-Benzyl-1-Methyl-2-Pyrrolidinone

N-Benzyloxycarbonyl phenylalanine methyl ester is reduced with DIBAL to the aldehyde using the procedure of Boger et al., *J. Med. Chem.* (1985) 28, 1779, which is homologated with the sodio derivative of trimethyl phosphonoacetate using the procedure of Wadsworth and Emmons, *Org. Synth.* (1965) 45, 44 to give methyl 4-(benzyloxycarbonyl)amino-5-phenyl-2-pentenoate.

Reduction and deprotection to give methyl 4-amino-5-phenylpentanoate is accomplished by treatment with 10% paladium on carbon in 5% acetic acid-ethanol under an atmosphere of hydrogen. Cyclization to 5-benzyl-2-pyrrolidinone occurs upon heating the free base in methanol solution. The title compound is obtained by deprotonation with NaH in DMF and methylation with methyl iodide.

H. 1,4-Dimethyl-2-Pyrrolidinone

3-Methyl-4-pentenoic acid is prepared from crotyl acetate using the ester enolate Claisen rearrangement described by Ireland et al, *J. Am. Chem Soc.* (1976) 98, 29688. The N-methyl amide derivative of the acid is then formed by reaction with DCC, DMAP, and methylamine, and the product is treated with ozone in methanol at −78° C. The ozonide is reduced with dimethyl sulfide to give 1,4-dimethyl-5-hydroxy-2-pyrrolidinone, with reductive removal of the hydroxyl group being accomplished with trifluoroacetic acid and triethylsilane to give the title compound.

I. 1,5,5-Trimethyl-2-Pyrrolidinone 5,5-Dimethyl-2-pyrrolidinone is prepared according to the method of Moffet, *Org. Synth. Coll.* Vol. IV (1963) 357, with the title compound being obtained by deprotonation with NaH in DMF and methylation with methyl iodide.

J. 1-Methyl-5,5-Tetramethylene-2-Pyrrolidinone

Nitrocyclopentane is prepared from bromocyclopentane using the method of Kornblum, *Org. Synth. Coll.* Vol. IV (1963) 724, and is added to methyl acrylate using the method of Moffet, *Org. Synth. Coll.* Vol. IV (1963), 652, to give methyl 3-(1-nitrocyclopentyl)-propanoate. Reduction and cyclization to give 5,5-tetramethylene-2-pyrrolidinone is accomplished by the method of Moffet, *Org. SYnth. Coll.* Vol. IV (1963), 357.

The title compound is then obtained by deprotonation with NaH in DMF and methylation with methyl iodide.

K. 1-(2-Benzyloxyethyl)-2-Pyrrolidinone

To a suspension of NaH (9.30 g of a 60% suspension in mineral oil; 233 mmol) in dry THF (300 mL) under an atmosphere of nitrogen was added a solution of 1-(2-hydroxyethyl)-2-pyrrolidinone (25.0 g; 194 mmol) in dry THF (25 mL) dropwise over a period of 10 min. The resulting mixture was stirred at room temperature for 3 hr., at which time it was cooled to 0° C. and benzyl bromide (39.7 g; 233 mmol) was added. The mixture was stirred overnight, allowing the cooling bath to warm to room temperature.

Acetic acid (2 mL) was added to quench any remaining NaH, and an equal volume of ether was added. After being cooled for several hours in a refrigerator, the precipitate was removed from the mixture by filtration and the filtrate was concentrated under reduced pressure. The resulting oil was flash chromatographed (SiO$_2$; 20% EtOAC/CH$_2$Cl$_2$) to give 1-(2-benzyloxyethyl)-2-pyrrolidinone as a colorless liquid (39.9 g; 94% yield).

L. 1-[3-(Benzyloxycarbonylamino)propyl]-2-Pyrrolidinone

To a 0° C. solution of 1-(3-aminopropyl)-2-pyrrolidinone (25.0 g; 176 mmol) and triethylamine (26.7 g; 264 mmol) in CH$_2$Cl$_2$ (500 mL) was added benzyl chloroformate (33.1 g; 194 mmol) dropwise over a period of 15 minutes. The mixture was stirred for 1.5 hr. at 0° C. and then for 15 hr. at ambient temperature, before the mixture was diluted with CH$_2$Cl$_2$ and extracted with 5% aqueous HCl (200 mL), H$_2$O (200 mL), and saturated aqueous NaHCO$_3$. The organic phase was dried (MgSO$_4$), filtered, and the solvents were removed under reduced pressure, then the oil which resulted was flash chromatographed (SiO$_2$; 2–5% MeOH/Ch$_2$Cl$_2$) to give the title compound as a colorless oil (42.7 g; 88% yield).

M. 1-[N-Benzyl-3-(Benzyloxycarbonyl)aminopropyl]-2-Pyrrolidinone

To a suspension of NaH (3.62 g of a 60% suspension in mineral oil; 90.6 mmol) in degassed DMF (300 mL) was added a solution of 1-[3-(benzyloxycarbonyl)aminopropyl]-2-pyrrolidinone (20.0 g; 72.5 mmol) in DMF (50 mL). The mixture was stirred at ambient temperature for 4 hr, cooled to 0° C., and to it was added benzyl bromide (14.9 g; 87.0 mmol).

The resulting mixture was stirred at 0° C. for 2 hr., and then at ambient temperature for 15 hr, before the mixture was diluted with an equal volume of ether and the salts were removed by filtration, and the solvents were removed under reduced pressure. The resulting oil was flash chromatographed (SiO$_2$; 2–5% MeOH/Ch$_2$Cl$_2$) to give the title compound as a colorless oil (22.3 g; 84% yield).

N. 1-Ethyl-3-(2-Pyrrolidinone-1-yl)piperidine

3-Amino-1-ethylpiperidine (1 equivalent) and δ-butyrolactone (4 equivalents) are heated together neat at 150° C. in a sealed vessel using the procedure of Zienty and Steahly, *J. Am. Chem. Soc.* (1947) 69, 715, and the title compound is obtained by vacuum distillation.

O. 1-(3-Picolyl)-2-Pyrrolidinone

3-Aminomethylpyridine (1 equivalent) and δ-butyrolactone (4 equivalents) are heated together neat at 150° C. in a sealed vessel and the title compound is obtained by vacuum distillation.

P. 1-(2-Diethylaminoethyl)-2-Pyrrolidinone 2-(Diethylamino)ethyl amine (1 equivalent) is heated to 150° C. in a sealed vessel with δ-butyrolactone (4 equivalents) and the title compound is obtained by vacuum distillation.

Q. 1-(2-Diethylaminoethyl)-5,5-Dimethyl-2-Pyrrolidinone 5,5-Dimethyl-2-pyrrolidinone obtained from the procedure in Example II is deprotonated with NaH in DMF solution, then allylated with allyl bromide to give 1-allyl-5,5-dimethyl-2-pyrrolidinone. Ozonolysis of the pyrrolidinone in MeOH solution at −78° C. and reduction using NaBH$_4$ gives 1-(2-hydroxyethyl)-5,5-dimethyl-2-pyrrolidinone, which is bromination with Ph$_3$P/CBr$_4$ in THF solution to give 1-(2-bromoethyl)-5,5-dimethyl-2-pyrrolidinone. Reaction with excess diethylamine in MeOH solution then gives the title compound.

EXAMPLE 2

Synthesis of Boc-(ACHP)-Lactams

A. Preparation of Boc-(ACHP)-1-Methyl-2-Pyrrolidinone

To a 0° C. solution of diisopropylamine (3.16 g; 31.3 mmol) in dry THF (100 mL) under an atmosphere of nitrogen was added n-butyllithium (19.3 mL of a 1.6 M solution in hexane; 30.8 mmol). After being stirred for 10 min., the resulting solution was cooled to −78° C., at which time a solution of 1-methyl-2-pyrrolidinone (3.07 g; 0.031 mmol) in dry THF (10 mL) was added dropwise over a period of 5 min. The resulting solution was then stirred at −78° C. for 1.5 hr., when a −78° C. solution of N-Boc-L-cyclohexyl-alaninal (7.5 g; 29 mmol), prepared according to the method of Boger, et al. *J. Med. Chem.* (1985) 28, 1779, in dry THF (50 mL) was added rapidly via cannula.

After being stirred for 5 minutes at −78° C., the reaction was quenched by the addition of 5 mL of water and the cooling bath was removed. More water (25 mL) and ether (125 mL) were added, the mixture was extracted with 5% aqueous HCl (150 mL), saturated with aqueous $NaHCO_3$ (150 mL), dried ($MgSO_4$), and filtered. Removal of the solvents under reduced pressure gave a viscous oil, from which the diasteriomeric aldol products were separated by flash chromatography ($SiO_2$; 2–5% MeOH/$Ch_2Cl_2$). The 2S, 3S, 4S diasteriomer crystallized from hexane, mp 120°–122° C. (1.74 g; 17% yield). The following compounds were obtained using the procedure given for the Preparation of Boc-(ACHP)-1-methyl-2-pyrrolidinone, above, and exhibited NMR spectra which support the assigned structure:

B. Boc-(ACHP)-1-Allyl-2-Pyrrolidinone
C. Boc-(ACHP)-5(S)-Benzyloxymethyl-1-Methyl-2-Pyrrolidinone
D. Boc-(ACHP)-1-Methyl-5(S)-Vinyl-2-Pyrrolidinone
E. Boc-(ACHP)-1-Methyl-5(R)-Vinyl-2-Pyrrolidinone
F. Boc-(ACHP)-1-(2-Benzyloxyethyl)-2-Pyrrolidinone
G. Boc-(ACHP)-1-[N-Benzyl-3-(Benzyloxycarbonylamino)-propyl]-2-Pyrrolidinone
H. Boc-(ACHP)-5(S) Methoxymethyl-1-Methyl-2 -Pyrrolidinone
I. Boc-(ACHP)-1-Cyclohexyl-2-Pyrrolidinone The following are obtained using the procedure given in Example 2A, except Examples 2J and 2K, which require an additional equivalent of LDA:

J. Boc-(ACHP)-5-(Hydroxymethyl,N-Isopropyl Urea)-1-Methyl-2-Pyrrolidinone
K. Boc-(ACHP)-1-[-3-Benzyloxycarbonylamino)-propyl]-2-Pyrrolidinone
L. Boc-(ACHP)-5-Fluoromethyl-1-Methyl-2-Pyrrolidinone
M. Boc-(ACHP)-5-Benzyl-1-Methyl-2-Pyrrolidinone
N. Boc-(ACHP)-1,4-Dimethyl-2-Pyrrolidinone
O. Boc-(ACHP)-1,5,5-Trimethyl-2-Pyrrolidinone
P. Boc-(ACHP)-1-(1-Ethylpiperidin-3-yl)-2-Pyrrolidinone
Q. Boc-(ACHP)-1-(3-Pyridylmethyl)-2-Pyrrolidinone
R. Boc-(ACHP)-1-(2-Diethylaminoethyl)-2-Pyrrolidinone
S. Boc-(ACHP)-1-(2-Diethylaminoethyl)-5,5-Dimethyl-2-Pyrrolidinone
T. Boc-(ACHP)-1-Methyl-5,5-Tetramethylene-2-Pyrrolidinone
U. Boc-(ACHP)-1-Phenyl-2-Pyrrolidinone
V. Synthesis and Further Transformations of Boc-(ACHP)-5-Iodomethyl-1-Methyl-2-Pyrrolidinone Boc-(ACHP)-5-benzyloxymethyl-1-methyl-2-pyrrolidinone is hydrogenolyzed using 10% palladium-on-carbon in 5% acetic acid-ethanol under 55 psig of hydrogen to give the 5-hydroxymethyl pyrrolidinone derivative. This derivative is then used for coupling to amino acids or may be converted to the title compound by iodination with $Ph_3P/I_2$/imidazole using the procedure of Garegg and Samuelson, *J. Chem. Soc.*, Perk. I (1980), 2866.

W. Boc-(ACHP)-5-Dimethylaminomethyl-1-Methyl-2 -Pyrrolidinone

The iodomethyl derivative from Example 2V above is treated with an excess of dimethylamine in methanol to give the title compound.

X. Boc-(ACHP)-5-Azidomethyl-1-Methyl-2-Pyrrolidinone

The iodomethyl derivative from Example 2 V is treated with sodium azide in DMSO solution to give the title compound.

Y. Boc-(ACHP)-5-Isovaleramidomethyl-1-Methyl-2-Pyrrolidinone

The azidomethyl derivative from Example 2X is treated with $Ph_3P$ using the procedure of Vaultier, et al., *Tetrahedron Letters* (1983) 24, 763 to give the aminomethyl derivative. Treatment of the latter with isovaleric anhydride in $CH_2Cl_2$ solution containing DMAP affords the title compound.

Z. Boc-(ACHP)-5-Aminomethyl-1-Methyl-2-Pyrrolidinone,N'-Isopropyl Urea

The aminomethyl derivative, produced as described in Example 2Y, above, is treated with 2-propylisocyanate in THF solution to give the title compound.

AA. Boc-(ACHP)-5-Aminomethyl-1-Methyl-2-Pyrrolidinone, Isopropyl Urethane

The aminomethyl derivative, produced as described in Example 2V above, is dissolved in $CH_2Cl_2$ and cooled to 0° C. Triethylamine (1.5 equivalents) and isopropyl chloroformate (1 equivalent) are added to give the title compound.

BB. Boc-(ACHP)-5-Methylthiomethyl-1-Methyl-2-Pyrrolidinone

The iodomethyl derivative, obtained as described in Example 2V, is treated with sodium methylmercaptide in THF solution, resulting in the title compound.

CC. Boc-(ACHP)-5-Methylsulfinylmethyl-1-Methyl-2-Pyrrolidinone

The methylthiomethyl derivative, produced as described in Example 2BB, is oxidized with one equivalent of MCPBA in chloroform solution at 0° C. to give the title compound.

DD. Boc-(ACHP)-5-Methylsulfonylmethyl-1-Methyl-2-Pyrrolidinone

The methylthiomethyl derivative, produced as described in Example 2BB, is oxidized with 2.5 equivalents of MCPBA in chloroform solution at room temperature to give the title compound.

EE. (ACHP)-1-Methyl-2-Pyrrolidinone-5-Carboxylic Acid

The hydroxymethyl derivative, produced as described in Example 2V, is converted to the t-butyldiphenylsilyloxymethyl derivative by treatment with chloro-t-butyldiphenylsilane (1 equivalent) in $CH_2Cl_2$ solution containing triethylamine (1 equivalent) and DMAP (0.1 equivalent). The OH- and NH-groups are protected by formation of an N,O-acetonide by treatment with 2-methoxypropene and PPTS (catalytic) in DMF solution, and the O-silyl protecting group is removed with TBAF in THF solution to give the hydroxymethyl derivative.

Oxidation with $Pt/O_2$ using the method of Saijo, et al, *Chem. Pharm. Bull.* (1980) 28, 1449, gives the N-Boc, N,O-acetonide of the title compound, which is used for subsequent reactions at the carboxyl center. Treatment with aqueous HCl in THF solution gives the title compound as the HCl salt.

FF. (ACHP)-1-Methyl-2-Pyrrolidinone-5-Isobutylcarboxamide

The N-Boc, N,O-acetonide carboxylic acid obtained from Example 2EE is activated with EDC and HOSU in $CH_2Cl_2$ solution and coupled with isobutylamine. The Boc and N,O-protecting groups are removed with HCl in ethanol to give the HCl salt of the title compound.

GG. (ACHP)-1-Methyl-2-Pyrrolidinone-5-Carboxylic Acid, Methyl Ester

The carboxylic acid obtained from Example 2EE above is treated with HCl in methanol to give the HCl salt of the title compound.

HH. Synthesis and Transformations of Boc-(ACHP)-1-(2-Iodoethyl)-2-Pyrrolidinone

Boc-(ACHP)-1-(2-benzyloxyethyl)-2-pyrrolidinone is hydrogenolyzed using 10% palladium-on-carbon in 5% acetic acid-ethanol under 55 psig of hydrogen to give Boc-(ACHP)-1-(2-hydroxyethyl)-2-pyrrolidinone. Treatment of the latter with $Ph_3/I_2$/imidazole, using the procedure of Garegg and Samuelson, *J. Chem. Soc., Perk I* (1980), 2866, affords the title compound.

II. Boc-(ACHP)-1-(2-Benzylthioethyl)-2-Pyrrolidinone

Treatment of the iodo derivative from Example 2HH with sodium benzylmercaptide in THF solution gives the title compound.

JJ. Boc-(ACHP)-1-(2-Benzylsulfinyl)-2-Pyrrolidinone

Treatment of the sulfide obtained from Example 2II with MCPBA (1 equivalent) in chloroform solution at 0° C. gives the title compound.

KK. Boc-(ACHP)-1-(2-Benzylsulfonylethyl)-2-Pyrrolidinone

Treatment of the sulfide obtained from Example 2II with MCPBA (2.5 equivalents) gives the title compound.

LL. Boc-(ACHP)-1-(2-Azidoethyl)-2-Pyrrolidinone

The iodo derivative obtained from Example 2II is heated with sodium azide in DMSO solution to give the title compound.

MM. Boc-(ACHP)-1-[-2-(3-Phenylpropanoyloxy)ethyl]-2-Pyrrolidinone

Boc-(ACHP)-1-(2-hydroxyethyl)-2-pyrrolidinone, obtained as described in Example 2II, is acylated at 0° C. in $CH_2Cl_2$ solution containing pyridine with 1 equivalent of 3-phenylpropanoyl chloride to give the title compound.

NN. Boc-(ACHP)-1-Carbomethoxymethyl-2-Pyrrolidinone

Boc-(ACHP)-1-allyl-2-pyrrolidinone is ozonolyzed using the oxidative workup described by Schreiber and Claus, *Org. Synth.* (1985) 64, 150, to give the title compound.

OO. Boc-(ACHP)-1-Carboxymethyl-2-Pyrrolidinone

The methyl ester obtained from Example 2NN above is saponified with lithium hydroxide in $THF/H_2O$ solution, acidified to pH3 and extracted with EtOAc to give the title compound.

PP Boc-(ACHP)-1-Carboxymethyl-2-Pyrrolidinone, 3-Aminoquinuclidine Amide

The carboxylic acid derivative obtained from Example 200 is activated in $CH_2Cl_2$ solution using DCC and HOSU to give the N-hydroxysuccinimide ester, which is then coupled in situ to 3-aminoquinuclidine to give the title compound.

EXAMPLE 3

Amino Acid Coupling Procedures and Subsequent Transformations

A. Preparation of Boc-Phe-His-(ACHP)-1-Methyl-2-Pyrrolidinone

Step 1. Boc-(DNP)His-(ACHP)-1-Methyl-2-Pyrrolidinone

To a solution of Boc-(ACHP)-1-methyl-2-pyrrolidinone (150 g; 4.24 mmol) in $CH_2Cl_2$ (3 mL) was added trifluoroacetic acid (3 mL) and the solution was stored under an atmosphere of nitrogen. After 45 min., excess TFA and solvent were removed under reduced pressure and the oil so obtained was triturated in ether, giving a white solid which was collected by filtration, washed with ether, and dried under reduced pressure.

The TFA salt (1.46 g; 93% yield) was dissolved under an atmosphere of nitrogen in a minimum amount of DMF (4-5 mL) (more ideally EtOAc would have been used if the salt had been soluble), and the solution was stored while the activation of Boc(DNP)His-OH was accomplished by in situ formation of a mixed anhydride, as described below.

(Activation of Boc(DNP)His-OH) To a suspension of Boc(DNP)His-OH (2.23 g; 5.30 mmol) in dry EtOAc (20 mL) under an atmosphere of nitrogen was added N-methylmorpholine (641μL; 5.83 mmol), which caused dissolution of any remaining solid. The solution was cooled to $-23°$ C., at which point isobutyl chloroformate (660μL); 5.09 mmol) was added, and the resulting solution was stirred at $-23°$ C. for 25 min. This activation accomplished, the DMF solution of the TFA salt was neutralized by the addition of N-methylmorpholine (560μL; 5.09 mmol) and was added via cannula to the cold solution of the mixed anhydride. After being stirred for 1 hr. at $-23°$ C., the reaction mixture was transferred to an ice-water bath and stirred for 1.5 hr. The cooling bath was removed and stirring of the mixture was continued for another 1.5 hr., at which time the reaction was quenched by the addition of water (20 mL).

The mixture was diluted with EtOAc (75 mL) and was washed successively with 5% aqueous HCl (100 mL), water (20 mL), and saturated aqueous $NaHCO_3$ (100 mL). The organic layer was dried ($MgSO_4$), filtered, and concentrated under reduced pressure to give an orange solid which was flash chromatographed ($SiO_2$; 3-5% $MeOH/CH_2Cl_2$) The coupling product was obtained as a yellow solid (2.08 g; 75% yield).

Step 2: Boc-Phe-(DNP)His-(ACHP)-1-Methyl-2-Pyrrolidinone

To a solution of the coupling product obtained from step 1 (2.08 g; 3.17 mmol) in $CH_2Cl_2$ (3 mL), was added trifluoroacetic acid (3 mL), and the mixture was stored under an atmosphere of nitrogen for 45 min. Excess TFA and solvent were removed under reduced pressure and the yellow oil so obtained was triturated in ether, with the solid which resulted being collected by filtration, washed with ether, and dried under reduced pressure.

The orange yellow solid (2.04 g; 96% yield) was dissolved under an atmosphere of nitrogen in dry EtOAc (10 mL) and stored while the activation of Boc-Phe-OH was accomplished by in situ formation of a mixed anhydride, as described below.

(Activation of Boc-Phe-OH) To a suspension of Boc-Phe-OH (1.05 g; 3.96 mmol) in dry EtOAc (15 mL) under an atmosphere of nitrogen was added N-methylmorpholine (479 μL; 4.35 mmol). The resulting solution was cooled to −23° C., isobutyl chloroformate (493 μL; 3.80 mmol) was added, and the solution was stirred for 25 min.

Following activation, the solution of the TFA salt was neutralized by the addition of N-methylmorpholine (383 uL; 3.49 mmol) and was added via cannula to the cold solution of the mixed anhydride. The resulting mixture was stirred at −23° C. for 1 hr., at 0° C. for 1.5 hr., and then at room temperature for 1.5 hr, and the reaction was quenched by the addition of water (25 mL), then diluted with EtOAc (75 mL). The organic phase was washed successively with 5% aqueous HCl (100 mL), water (20 mL), and saturated aqueous NaHCO$_3$ (75 mL), then dried (MgSO$_4$), and filtered.

Removal of the solvent under reduced pressure gave a solid which was flash chromatographed (SiO$_2$; 4–7% MeOH/CH$_2$Cl$_2$) The coupling product was obtained as a yellow solid (2.24 g; 88% yield).

Step 3: Boc-Phe-His-(ACHP)-1-Methyl-2-Pyrrolidinone

The coupling product obtained from step 2 (2.24 g; 2.79 mmol) was dissolved under an atmosphere of nitrogen in dry CH$_2$Cl$_2$ (5 mL), and thiophenol (3 mL) was added, followed by N-methylmorpholine (30μL; 0.27 mmol). The mixture was stirred at room temperature for 5 hr., at which time the solvent and excess thiophenol were removed under reduced pressure (0.2 torr) at 30° C.. The residue was flash chromatographed (SiO$_2$; 5–10% MeOH/CH$_2$Cl$_2$), giving the deprotected product as an off-white powder (1.53 g; 86% yield).

The title compound exhibited satisfactory NMR spectral properties, was analyzed for purity by reverse phase HPLC (C$_{18}$ column, 5% acetonitrile-water to 95% acetonitrile-water, buffered with 0.1% H$_3$PO$_4$; 30 min. gradient) and was analyzed for composition by C, H, and N combustion analysis. In vitro inhibition of human plasma renin was measured as described by Boger, et al., *J. Med. Chem.* (1985) 28, 1779. IC$_{50}$=9.9 nM.

B. Preparation of Boc-Phe-His-(ACHP)-1-Cyclohexyl-2-Pyrrolidinone (Dipeptide Fragment Coupling Methodology)

Into a 0° C. solution of Boc-(ACHP)-1-cyclohexyl-2-pyrrolidinone (0.750 g; 1.78 mmol) in EtOAc (100 mL) was bubbled HCl gas for 20 min. Excess HCl was purged from the solution by bubbling nitrogen through it for 30 min. and the solution was warmed to room temperature. EtOAc was removed under reduced pressure and the residue was triturated with ether and the white solid which resulted was collected by suction filtration and dried in vacuo (606mg; 95% yield).

The salt was then dissolved in dry CH$_2$Cl$_2$ (10 mL) and neutralized by the addition of triethylamine (189 mg; 1.78 mmol), with the resulting solution being added via cannula to a solution of activated ester.

(Preparation of activated ester) To a 020 C. solution of Boc-Phe-(DNP)His-OH (1.112 g; 1.96 mmol) in dry CH$_2$Cl$_2$ (10 mL) under an atmosphere of nitrogen were sequentially added N-hydroxysuccinimide (248mg; 2.16 mmol), and EDC (376 mg; 1.96 mmol). After being stirred at 0° C. for 30 min, the solution of neutralized amine salt was added and the mixture was allowed to warm to room temperature and stirred for 24 hrs. The solution was partitioned between CH$_2$Cl$_2$ and 5% aqueous HCl and the organic phase was washed with saturated aqueous NaHCO$_3$, then dried (MgSO$_4$), and filtered. The solvent was removed under reduced pressure and the residue was flash chromatographed (SiO$_2$; 3%MeOH/Ch$_2$Cl$_2$) to give the coupling product as a pale yellow foam (1.16 g; 75%).

Treatment with thiophenol as described above in Method A, step 3, and purification using flash chromatography (SiO$_2$; 7%MeOH/CH$_2$Cl$_2$) followed by crystallization from MeOH gave the title compound as small white needles, mp 110°–112° C. (680 mg; 84% yield). The title compound exhibited satisfactory NMR spectral properties, was analyzed by HPLC as described above and by C, H, and N combustion analysis. IC$_{50}$=10.0 nM.

The following peptides were produced using the method of Example 3A, and exhibited satisfactory NMR spectra. They were analyzed for purity by HPLC (30 minute gradient, 5% CH$_3$CN—H$_2$O to 95% CH$_3$CN—H$_2$O buffered with 0.1% H$_3$PO$_4$; C$_{18}$ reverse phase column), and were analyzed for composition by C, H, and N combustion analysis. IC$_{50}$ values were measured in vitro using the human plasma renin assay, as described by Boger et al. *J. Med. Chem.* (1985) 28, 1779.

C. Boc-Phe-His-(ACHP)-5(S)-Benzyloxymethyl-1-Methyl-2-Pyrrolidinone

IC$_{50}$=4.4 μM

D. Boc-Phe-His-(ACHP)-5(S)-Methoxymethyl-1-Methyl-2-Pyrrolidinone

IC$_{50}$=71 M

E. Boc-Phe-His-(ACHP)-1-(2-Benzyloxyethyl-2-Pyrrolidinone

IC$_{50}$=24nM

F. Boc-Phe-His-(ACHP)-1-Methyl-5(S)-Vinyl-2-Pyrrolidinone

IC$_{50}$=8.0 nM

G. Boc-Phe-His-(ACHP)-1-Methyl-5(R)-Vinyl-2-Pyrrolidinone

IC$_{50}$=2.5 nM

The following peptides were produced by further transformation of Examples 3C, 3E, 3F, and 3G, and exhibited satisfactory NMR spectra. They were analyzed for purity by HPLC under conditions given above, and were analyzed for composition by C, H, and N combustion analysis. IC$_{50}$ values were measured as described above.

H. Boc-Phe-His-(ACHP)-1-(2-Hydroxyethyl)-2-Pyrrolidinone

To a solution of Boc-Phe-His-(ACHP)-1-(2-Benzyloxyethyl)-2-pyrrolidinone (360mg; 0.475 mmol) in 20 mL of 10:1 MeOH/HOAc was added 10% palladium-on-carbon (150 mg) and the resulting suspension was shaken on a Parr apparatus which was pressurized with hydrogen (55 psig) for 16 hrs. The catalyst was removed by filtration and was washed with methanol. The filtrate solvents were removed under reduced pressure (ca. 1 torr) at room temperature on a rotovap and the residue was passed through a short column of SiO$_2$ using 8% MeOH/Ch$_2$Cl$_2$. The product alcohol was obtained as a white powdery solid (221 mg; 70% yield). IC$_{50}$=7.7 nM.

I. Boc-Phe-His-(ACHP)-5(S)-Hydroxymethyl)-1-Methyl-2-Pyrrolidinone

To a solution of Boc-Phe-His-(ACHP)-5(S)-benzyloxymethyl-1-methyl-2-pyrrolidinone (320 mg; 0.422 mmol) in 20 mL of 10:1 MeOH/HOAc was added 10% palladium-on-carbon (160 mg), and the resulting suspension was shaken on a Parr apparatus pressurized with hydrogen (55 psig) for 18 hrs. The catalyst was removed by filtration and was washed with MeOH.

The filtrate solvents were removed under reduced pressure on a rotovap (ca. 1 torr) at room temperature and the residue was passed through a short column of $SiO_2$ (8% $MeOH/CH_2Cl_2$). The product alcohol was obtained as a white solid (191 mg; 68% yield). $IC_{50}=14$ nM.

J. Boc-Phe-His-(ACHP)-5(S)-Acetoxymethyl)-1-Methyl-2-Pyrrolidinone

To a solution of Boc-Phe-His-(ACHP)-5(S)-hydroxymethyl-1-methyl-2-pyrrolidinone (74 mg; 0.11 mmol) in dry DMF (0.06 mL) under an atmosphere of nitrogen was added NaOAc (45 mg; 0.55 mmol) and acetic anhydride (28μL; 0.30 mmol). The resulting suspension was stirred at room temperature for 3 hrs., at which time triethylamine (84uL; 0.60 mmol) and water (50uL) added.

After being stirred at room temperature for 4 hr., the volatile components were removed under pressure (0.2 torr), and the residue was passed through a short $SiO_2$ column (6% $MeOH/CH_2Cl_2$). The product was obtained as a white solid (55 mg; 70% yield). $IC_{50}=157$ nM.

K. Boc-Phe-His-(ACHP)-5(R)-Ethyl-1-Methyl-2-Pyrrolidinone

To a solution of Boc-Phe-His-(ACHP)-5(S)-vinyl-1-methyl-2-pyrrolidinone (86 mg; 0.13 mmol) in MeOH (10 mL) was added 10% palladium-on-carbon (45 mg). The resulting suspension was stirred at room temperature under an atmosphere of hydrogen (1 atm) for 8 hr. The catalyst was removed by filtration and was washed with MeOH. The filtrate solvent was removed under reduced pressure, giving an oil which was passed through a short column of $SiO_2$ (7% $MeOH/CH_2Cl_2$).

The product was obtained as a white solid (78 mg; 91% yield). $IC_{50}=8.5$ nM.

L. Boc-Phe-His-(ACHP)-5(S)-Ethyl-1-Methyl-2-Pyrrolidinone

Hydrogenation of the-5(R)- vinyl derivative using the procedure from Example 3K above gave the title compound (88%) $IC_{50}=5.3$ nM.

Other examples of lactam modification after the peptide segment has been attached are given by the following examples.

M. Boc-Phe-His-(ACHP)-1-(3-Aminopropyl)-2-Pyrrolidinone

Boc-Phe-His-(ACHP)-1-[3-(benzyloxycarbonylamino) propyl]-2-pyrrolidinone is treated with 10% palladium-on-carbon in 4% $HCO_2H$-MeOH to remove the CBZ group. Neutralization by partitioning between $CH_2Cl_2$ and aqueous $NaHCO_3$ gives the title compound.

N. Boc-Phe-His-(ACHP)-1-(3-Acetamidopropyl)-2-Pyrrolidinone

The aminopropyl derivative obtained from Example 3H above is acylated in DMF solution containing pyridine with acetic anhydride (2.5 equivalents). The acetyl group is removed from the histidine side chain in situ by the addition of $H_2O$ and triethylamine, giving the title compound. Ipoc-Phe-His- peptides are made using sequential coupling, using Ipoc-Phe instead of Boc-Phe, in the method according to Example 3A, or by fragment coupling, using Ipoc Phe-His in place of Boc-Phe-His, in the method according to Example 3B.

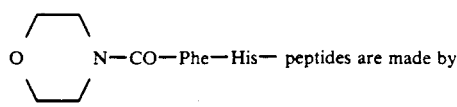

peptides are made by sequential coupling using mixed anhydride coupling according to Example 3A for the histidine group, and using mixed anhydride or DCC/HOBT coupling for the

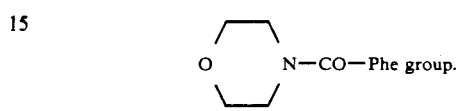

group.

$(CH_3)_2CH-SO_2$-Phe-His- peptides are made by sequential coupling using mixed anhydride coupling according to Example 3A for the histidine group, and using mixed anhydride or DCC/HOBT coupling for the $(CH_3)_2CH-SO_2$-Phe group.

$(CH_3)_3C-SO_2-CH_2-CH(CH_2Ph)-CO$-His- peptides are made by sequential coupling using mixed anhydride coupling according to Example 3A for the histidine group and DCC/HOBT or DCC/HOSU coupling for the $(CH_3)_3C-SO_2-CH_2-CH(CH_2Ph)-CO-$ group.

2-Indolyl-CO-His- peptides are made by sequential coupling using mixed anhydride coupling according to Example 3A for the histidine group, and DCC or EDC coupling of indole-2-carboxylic acid.

These methods are applied to any of the 42 Boc-(ACHP)-lactams described in Example 2.

The following examples are illustrative of the methods for producing quaternary ammonium salts. Purification of these compounds is accomplished using preparative reverse phase HPLC, using acetonitrile water containing 0.1% TFA as an eluent. The final products are obtained as acetate salts by passage through an ion exchange column (Bio-Rad AG3-X4A resin, acetate form).

O. Boc-Phe-His-(ACHP)-1-[2-(Quinuclidin-1-yl)-ethyl]-2-Pyrrolidinone Acetate

Boc-Phe-His-(ACHP)-1-(2-hydroxyethyl)-2-pyrrolidinone is brominated by treatment with $Ph_3P/CBr_4$ in THF solution to give Boc-Phe-His-(ACHP)-1-(2-bromoethyl)-2-pyrrolidinone. Reaction of the latter with quinuclidine in DMF solution gives the quaternary ammonium bromide salt, with purification and ion exchange, as described above, giving the title compound.

P. Boc-Phe-His-(ACHP)-1-[N-Benzyl-3-(Dimethylamino)-propyl]-2-Pyrrolidinone Acetate To a stirred suspension of 10% palladium-on-carbon (0.60 g) in 4% formic acid-methanol (100 mL) was added a solution of Boc-Phe-His-(ACHP)-1-[N-benzyl-3-(benzyloxycarbonylamino)propyl]-2pyrrolidinone (1.10 g; 1.22 mmol) in methanol (10 mL) and the mixture was stirred for 1.5 hr. at ambient temperature. The catalyst was filtered through Celite and washed with methanol and the filtrate solvents were removed under reduced pressure, with the residue being partitioned between $CH_2Cl_2$ and saturated aqueous $NaHCO_3$.

The aqueous phase was extracted with $CH_2Cl_2$ and the combined organic phases were dried ($MgSO_4$) and filtered. The solvent was removed under reduced pressure and the residue was purified by preparative reverse phase HPLC (gradient elution using 95/5 to 2/98 water/acetonitrile). Trituration in ether gave Boc-Phe-His-(ACHP)-1-(3-benzylaminopropyl)-2-pyrrolidinone as an amorphous white solid (0.674 g; 68 g).

Treatment of this amine in DMF containing 1.5 equivalents of DIPEA with 2.2 equivalents of methyl iodide, followed by purification and ion exchange as described above, gave the title compound.

Q. Ipoc-Phe-His-(ACHP)-1-[N-Benzyl-2-(Dimethylamino)ethyl[-5,5-Dimethyl-2-Pyrrolidinone Acetate Ipoc-Phe-His-(ACHP)-1-(2-diethylaminoethyl)-5,5-dimethyl-2-pyrrolidinone is protected on the histidine side chain with (Boc)$_2$O in DMF solution. Benzyl bromide (1 equivalent) is then added and the solution is warmed to 50° C.

When the reaction is complete by TLC, H$_2$O and Et$_3$N (5 equivalents each) are added to remove the Boc group, with purification and ion exchange, as described above, giving the title compound.

R. Boc-Phe-His-(ACHP)-1-[(1-Methylquinuclidin-3-yl)-Carboxamido-Methyl-2-Pyrrolidinone Acetate Boc-(ACHP)-lactam from Example 2P is converted to the Boc-Phe-His-(ACHP)-lactam derivative using the methods of Example 3A or 3B and is then methylated on the quinuclidine 1-position by treatment with methyl iodide (1 equivalent) in DMF solution. Purification and ion exchange, as described, gives the title compound.

Claims to the invention follow.

What is claimed is:

1. A peptide of the formula:

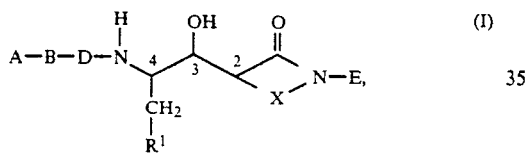

wherein:
A is hydrogen;
C$_1$-C$_6$-alkyl;
aryl, where aryl is unsubstituted or mono-, di- or trisubstituted phenyl, wherein the substituent(s) is/are independently selected from the group consisting of C$_1$-C$_7$-alkyl, phenyl-C$_1$-C$_4$-alkyl, amino, mono- or di-C$_1$-C$_4$-alkylamino, amino-C$_1$-C$_4$-alkyl, hydroxy-C$_1$-C$_4$-alkyl, mono- or di-C$_1$-C$_4$-alkylamino- C$_1$-C$_4$-alkyl, guanidyl, guanidyl-C$_1$-C$_4$-alkyl, hydroxyl, C$_1$-C$_4$-alkoxy, trifluoromethyl, halo, CHO, —CO$_2$H, —CONH$_2$, —CONH—C$_1$-C$_4$-alkyl, —CON(C$_1$-C$_4$-alkyl)$_2$, —CO—C$_1$-C$_4$-alkyl —(CH$_2$)$_m$—$^\oplus$N(R$^3$)$_2$R$^4$ A$^\ominus$, where R$^3$ is C$_1$-C$_4$-alkyl, —(CH$_2$)$_4$—, —(CH$_2$)$_5$— or —(CH$_2$)$_2$—O—(CH$_2$)$_2$—; R$^4$ is C$_1$-C$_4$-alkyl, C$_1$-C$_4$-hydroxyalkyl, C$_1$-C$_4$-carboxyalkyl, or —CH$_2$-phenyl; A$^\ominus$ is a counterion selected from the group consisting of single negatively-charged ions, and m is 0-to-3; —CO$_2$—C$_1$-C$_4$-alkyl, —CO$_2$—C$_1$-C$_4$-alkoxy-C$_2$-C$_4$-alkyl,

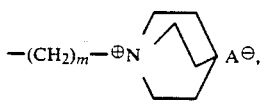

where A$^\ominus$ and m are as defined above, and —NR$^5$R$^6$, where R$^5$ and R$^6$ are independently hydrogen, unsubstituted or monosubstituted C$_1$-C$_4$-alkyl, wherein the substituent is amino, mono- or di-C$_1$-C$_4$-alkylamino or —$^\oplus$N(R$^3$)$_2$R$^4$ A$^\ominus$, where R$^3$, R$^4$ and A$^\ominus$ are as defined above;

Het, where Het is an unsubstituted or mono- or disubstituted 5-to-7-membered mono- or bicyclic or 7- to 10- membered bicyclic heterocyclic ring, where the one or two heteroatoms are independently selected from the group consisting of N, O, S, NO, SO, SO$_2$ or quaternized N, and the substituent(s) is/are independently selected from the group consisting of hydroxyl, thiol, C$_1$-C$_6$-alkyl, CF$_3$, C$_1$-C$_4$-alkoxy, halo, aryl, as defined above, aryl-C$_1$-C$_4$-alkyl, amino, mono- or di-C$_1$-C$_4$-alkylamino, amino-C$_1$-C$_4$-alkyl, hydroxy-C$_1$-C$_4$-alkyl, mono- or di-C$_1$-C$_4$-alkylamino-C$_1$-C$_4$-alkyl, guanidyl, guanidyl-C$_1$-C$_4$-alkyl, CHO, CO$_2$H, CO$_2$—C$_1$-C$_4$-alkyl, CONH$_2$, CONH—C$_1$-C$_4$-alkyl, CON(C$_1$-C$_4$-alkyl)$_2$, NR$^5$R$^6$,

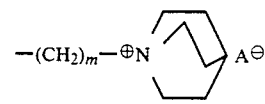

and —(CH$_2$)$_m$—$^\oplus$N(R$^3$)$_2$R$^4$ A$^\ominus$, wherein R$^5$, R$^6$, A$^\ominus$, m, R$^3$ and R$^4$ are as defined above, or when the heteroatom N is present, the substituents are alternatively —(CH$_2$)$_q$— or —(CH$_2$)$_2$—O—(CH$_2$)$_2$— and form a ring with the N-atom, wherein q is 3-to-6;

where R$^2$ is C$_1$-C$_7$-alkyl; hydrogen; Het, as defined above; aryl, as defined above; mono-substituted C$_1$-C$_5$-alkyl, wherein the substituent is selected from the group consisting of aryl, as defined above; Het, as defined above; hydroxyl; —CO$_2$H; CO$_2$R$^7$, where R$^7$ is C$_1$-C$_5$-alkyl, aryl, as defined above, and aryl-C$_1$-C$_4$-alkyl; CONH$_2$; —CONH—R$^7$ or —S(O)$_n$—R$^7$, wherein n is 0-to-2 and R$^7$ is as defined above; C$_1$-C$_4$-alkoxy; C$_3$-C$_7$-cycloalkyl; amino; mono- or di-C$_1$-C$_4$-alkylamino; —NH-aryl, —NH—CH$_2$-aryl or —CO-aryl, where aryl is as defined above; and —NH-Het, —NH—CH$_2$-Het or —CO-Het, where Het is as defined above;

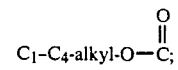

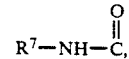

where R$^7$ is as defined above; or

where R$^9$ is C$_1$-C$_5$-alkyl, aryl, as defined above, or Het, as defined above:

B and D are independently

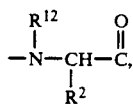

where $R^{12}$ is hydrogen, $C_1-C_5$-alkyl or $CH_2$-aryl, wherein aryl is as defined above; and $R^2$ is as defined above;

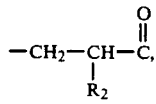

where $R^2$ is as defined above; or either B or D, but not both simultaneously, is absent;
$R^1$ is hydrogen;
$C_3-C_6$-alkyl;
aryl, as defined above;
unsubstituted, mono-, di- or trisubstituted $C_3-C_7$-cycloalkyl, where the substituent(s) is/are selected from the group consisting of $C_1-C_4$-alkyl, trifluoromethyl, hydroxyl, $C_1-C_4$-alkoxy and halo; or
unsubstituted or 4-monosubstituted 1,3-dithiolan-2-yl or unsubstituted or 4-monosubstituted 1,3-dithian-2-yl, where the substituent is —$(CH_2)_m$-aryl, where m and aryl are as defined above;
X is

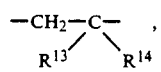

where and $R^{13}$ and $R^{14}$ are independently hydrogen; $C_1-C_7$-alkyl; $C_2-C_7$-alkenyl; —$CO_2H$; —$CONH_2$; —$CO_2R^7$; —CO—NH—$R^7$ or —CO—N$(R^7)_2$, wherein $R^7$ is as defined above; monosubstituted $C_1-C_5$-alkyl, wherein the substituent is selected from the group consisting of azido; halo; hydroxy; $C_1-C_5$-alkoxy; aryl, aryl—$CH_2O$—, aryloxy, aryl-COO—, aryl-$CH_2$—NH— or arylamino, where aryl is as defined above; $C_1-C_5$-alkyl-$CO_2$—; $R^7$NH—COO—, $R^7$—CO—NH—, $R^7$—NH—CO—NH— or $R^7$—$S(O)_n$, where n and $R^7$ are as defined above; amino; mono- or di-$C_1-C_4$-alkylamino; or Het, as defined above; or $R^{13}$ and $R^{14}$ are connected to form a polymethylene chain of the formula, —$(CH_2)_p$, where p is 2-to-6; or

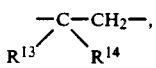

where $R^{13}$ and $R^{14}$ are as defined above; and
E is hydrogen;
aryl, as defined above;
Het, as defined above;
$C_2-C_7$-alkenyl; or unsubstituted or mono- substituted $C_1-C_7$-alkyl or unsubstituted or mono-substituted $C_3-C_7$-cycloalkyl, where the substituent is selected from the group consisting of aryl, —CO-aryl, —NH-aryl or —O-aryl, wherein aryl is as defined above; Het, —NH-Het, —O-Het, —CO-Het, —NH—CO-Het, CO—NH-Het, —CO—NH—$CH_2$-Het or O—CO—Het, wherein Het is as defined above; azido; $C_3-C_7$-cycloalkyl; halo; hydroxyl; $C_1-C_4$-alkoxy; —COOH; —O—CO—$R^7$, —O—CO—NH—R , —NH—CO—$R^7$, —NH—CO—NH—$R^7$, —$S(O)_n$—$R^7$, —$CO_2R^7$ or —CO—NH—$R^7$, wherein $R^7$ and n are as defined above; amino; mono- or di-$C_1-C_4$-alkylamino; —CHO; and —$^\oplus N(R^3)_2 R^8 A^\ominus$,

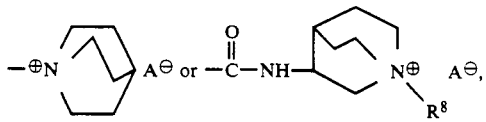

where $R^8$ is $C_1-C_4$-alkyl, $C_1-C_4$-hydroxyalkyl, alkyl, $C_1-C_4$-carboxyalkyl, —$CH_2$-aryl, wherein aryl is as defined above, or —$CH_2$—Het, wherein Het is as defined above, and $R^3$ and $A^\ominus$ are as defined above;
or a pharmaceutically-acceptable salt thereof.

2. A peptide according to claim 1, wherein A is $R^2$—CO—, $R^9$—$SO_2$—, $C_1-C_4$-alkyl-O—CO-13 or $R^7$—NH—CO—, where $R^2$, $R^7$ and $R^9$ are as defined in claim 1; B is absent when D is L-histidyl or L-valinyl, or B is unsubstituted or monosubstituted L-phenylalanyl where the substituent is on the phenyl ring and is para-methoxy, or

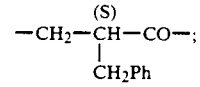

D is absent, when B is unsubstituted or monosubstituted L-phenylalanyl or L-histidyl or L-valinyl; $R^1$ is cyclohexyl; X is

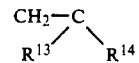

wherein, $R^{13}$ and $R^{14}$ are simultaneously or independently hydrogen, methyl, ethenyl or ethyl; and E is $C_1-C_6$-alkyl, —$(CH_2)_r$—$^\oplus N$—$(R^3)_2R^8$ $CH_3CO_2^\ominus$, wherein r is 2 or 3 and $R^3$ and $R^8$ are as defined in claim 1,

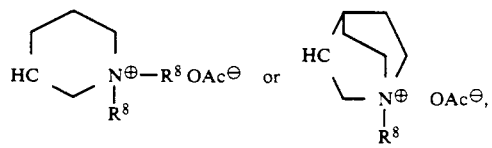

wherein $R^8$ is as defined in claim 1.

3. A peptide according to claim 1, wherein in the formula:

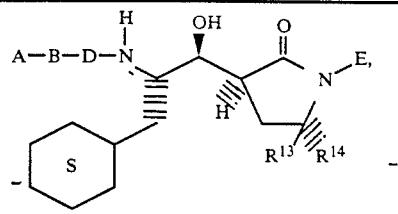

| A | B | D | R¹³ | R¹⁴ | E |
|---|---|---|---|---|---|
| (CH₃)₃C—CO— | Phe | His | H | H | n-Bu |
| " | " | " | " | " | —CH₂—CH(CH₃)₂ |
| " | " | " | " | " | —CH₂—CH(CH₃)—CH₂CH₃ |
| " | " | " | —CH=CH₂ | " | n-Bu |
| " | " | " | —CH₃ | " | " |
| " | " | " | " | —CH₃ | " |
| (CH₃)₂CH—SO₂— | " | " | " | " | " |
| ⟨morpholine⟩N—CO— | " | " | " | " | " |
| — | ⟨indole-2-CO—⟩ | " | " | " | " |
| (CH₃)₂CH—SO₂— | (S) —CH₂—CH(CH₂Ph)—CO— | His | —CH₃ | —CH₃ | n-Bu |
| (CH₃)₃C—CO— | Phe | " | " | " | (CH₂)₂—N⁺(Et)₂CH₂Ph  OAc⁻ |
| (CH₃)₂CH—SO₂— | " | " | " | " | " |
| " | (S) CH₂CH(CH₂Ph)—CO— | " | " | " | " |
| " | " | Val | " | " | " |
| ⟨morpholine⟩N—CO— | Phe | His | " | " | " |
| (CH₃)₃C—CO— | " | " | " | " | (CH₂)₃N⁺(Et)₂—CH₂Ph  OAc⁻ |
| (CH₃)₂CH—SO₂— | " | " | " | " | " |
| " | (S) CH₂CH(CH₂Ph)—CO— | " | " | " | " |
| " | " | Val | " | " | " |
| ⟨morpholine⟩N—CO— | Phe | His | " | " | " |
| (CH₃)₃C—CO— | Phe | His | H | H | —HC⟨piperidine-N⁺(Et)₂⟩ OAc⁻ |

-continued

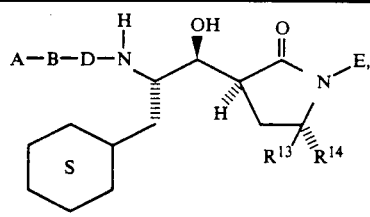

| A | B | D | $R^{13}$ | $R^{14}$ | E |
|---|---|---|---|---|---|
| $(CH_3)_2CH-SO_2-$ | " | " | " | " | " |
| " | (S) −CH₂CH−CO− \| CH₂Ph | His | " | " | " |
| " | " | Val | " | " | " |
| morpholine-N-CO− | " | Phe | His | " | " | " |
| $(CH_3)_3C-CO-$ | " | " | " | " | HC⟨piperidine⟩N⊕(CH₂Ph)Ph  ⊖OAc |
| $(CH_3)_2CH-SO_2-$ | " | " | " | " | " |
| " | (S) CH₂CH−CO− \| CH₂Ph | " | " | " | " |
| morpholine-N-CO− | " | Phe | " | " | " |
| − | indole-CH=CH-CO− | His | H | H | HC⟨piperidine⟩N⊕Ph  ⊖OAc |
| − | " | " | " | " | −HC⟨piperidine⟩N⊕(Et)₂  ⊖OAc |
| − | " | " | $-CH_3$ | $-CH_3$ | $-(CH_2)_3-\overset{\oplus}{N}(Et)_2CH_2Ph$  $OAc^{\ominus}$ |
| − | " | " | " | " | $-(CH_2)_2\overset{\oplus}{N}(Et_2)CH_2Ph$  $OAc^{\ominus}$ |

4. A peptide according to claim 1, wherein in the formula:

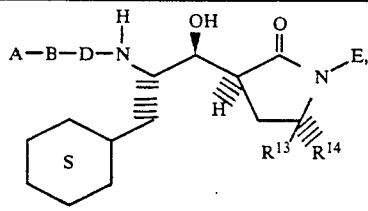

| A | B | D | R¹³ | R¹⁴ | E |
|---|---|---|---|---|---|
| BOC | Phe | His | H | H | —(CH₂)₂N⊕(Et)₂CH₃⊖OAc |
| Ipoc | " | " | " | " | " |
| (CH₃)₂CH—SO₂ | " | " | " | " | " |
| " | (S) CH₂CH—CO— \| CH₂Ph | " | " | " | " |
| Boc | Phe | " | CH₃ | CH₃ | " |
| Ipoc | " | " | " | " | " |
| (CH₃)₂CH—SO₂ | " | " | " | " | " |
| " | (S) CH₂CH—CO— \| CH₂Ph | " | " | " | " |
| " | " | " | " | " | n-Bu |
| Boc | Phe | His | H | H | —HC⟨cyclohexyl-N(Et)₂⊕⟩ ⊖OAc |
| Ipoc | Phe | His | H | H | —CH⟨cyclohexyl-N(Et)₂⊕⟩ ⊖OAc |
| (CH₃)₂CH—SO₂ | " | " | " | " | " |
| " | (S) CH₂CH—CO— \| CH₂Ph | " | " | " | " |

5. A pharmaceutical composition for renin-associated hypertension or congestive heart failure comprising a pharmaceutical carrier and a therapeutically-effective amount of a peptide according to claim 1.

6. A pharmaceutical composition according to claim 5, also comprising an adjuvant.

7. A method of treating renin-associated hypertension or congestive heart failure in mammals comprising administering a therapeutically-effective amount of a peptide according to claim 1.

8. A method according to claim 7, wherein mammals are human and the therapeutically-effective amount is from 0.02 to 10 grams per day.

9. A method of diagnosing renin as a contributory factor in hypertension or congestive heart failure comprising administering to a patient from 0.1 to 10 mg/kg of body weight of the patient a peptide according to claim 1 and monitoring the patient's blood pressure for a transitory fall that would indicate supranormal plasma renin level.

* * * * *